US007521529B2

(12) United States Patent
Hillman et al.

(10) Patent No.: US 7,521,529 B2
(45) Date of Patent: Apr. 21, 2009

(54) DIFFERENTIALLY PROTECTED ORTHOGONAL LANTHIONINE TECHNOLOGY

(75) Inventors: Jeffrey D. Hillman, Gainesville, FL (US); Ravi S. Orugunty, Alachua, FL (US); James L. Smith, Alachua, FL (US)

(73) Assignee: Oragenics, Inc., Alachua, FL (US)

( * ) Notice: Subject to any disclaimer, the term of this patent is extended or adjusted under 35 U.S.C. 154(b) by 0 days.

(21) Appl. No.: 11/502,805

(22) Filed: Aug. 11, 2006

(65) Prior Publication Data

US 2007/0037963 A1     Feb. 15, 2007

Related U.S. Application Data

(63) Continuation-in-part of application No. PCT/US06/31510, filed on Aug. 11, 2006.

(60) Provisional application No. 60/808,907, filed on May 26, 2006, provisional application No. 60/708,086, filed on Aug. 12, 2005.

(51) Int. Cl.
*A61K 38/12* (2006.01)
*A61K 38/16* (2006.01)
*C07K 1/02* (2006.01)
*C07K 5/12* (2006.01)
*C07K 14/195* (2006.01)

(52) U.S. Cl. .................. 530/324; 530/300; 530/302; 530/307; 530/315; 530/317; 530/333; 514/11; 514/12; 514/14; 514/15; 514/16; 514/17

(58) Field of Classification Search ................ None
See application file for complete search history.

(56) References Cited

U.S. PATENT DOCUMENTS

| 5,049,656 | A | 9/1991 | Lewis et al. |
| 5,221,736 | A | 6/1993 | Coolidge et al. |
| 5,256,549 | A | 10/1993 | Urdea et al. |
| 5,521,184 | A | 5/1996 | Zimmermann |
| 6,268,339 | B1 * | 7/2001 | Goodman et al. ............. 514/11 |
| 2004/0072333 | A1 | 4/2004 | Coughlin et al. |
| 2005/0164339 | A1 | 7/2005 | van der Donk et al. |

OTHER PUBLICATIONS

Zhu, et al., "Efficient Synthesis of Differently Protected Lanthionines via β-Bromoalanine Derivatives", Eur. J. Org. Chem. P. 4069-4072 (2003).
Alberico, "Orthogonal Protecting Groups for Nº-Amino and C-Terminal Carboxyl Functions in Solid-Phase Peptide Sythesis", Biopolymers, vol. 55, p. 123-139 (2000).
Miyake, et al., "Enantioselective conversion of meso-cyclic disulfides to chiral cyclic sulfides via desulfurization with chiral aminophosphines", J. Chem. Soc., Perk Trans. 1, p. 1595-1599 (2000).

Mustapa, et al., "Synthesis of orthogonally protected lanthionines: a reassessment of the use of alanyl β-cation equivalents", Tetrahedron Letters, 43, p. 8359-8362 (2002).
Kupke, et al., "Purification and Characterization EpiD, a Flavoprotein Involved in the Biosynthesis of the Lantibiotic Epidermin", Journal of Bacteriology, vol. 174, No. 16, p. 5354-5361 (1992).
Kupke, et al., "Mass Spectroscopic Analysis of a Novel Enzymatic Reaction", The Journal of Biological Chemistry, vol. 269, No. 8, p. 5653-5659 (1994).
Kupke, et al., "Oxidative Decarboxylation of Peptides Catalyzed by Flavoprotein EpiD", The Journal of Biological Chemistry, vol. 270, No. 19, p. 11282-11289 (1995).
Kupke, et al., "The Enethiolate Anion Reaction Products of EpiD", The Journal of Biological Chemistry, vol. 272, No. 8, p. 4759-4762 (1997).
Merrifield, "Solid Phase Peptide Synthesis", The Synthesis of a Tetrapeptide, p. 2149-2154 (1963).
Olah, et al., "Chlorotrimethylsilane/Lithium Bromide and Hexamethyldisilane/Pyridinium Bromide Perbromide: Effective and Selective Reagents for the Conversion of Alkyl (Cycloalky and Aralkyl) Alcohols in to Bromides", J. Org. Chem., 45, p. 1638-1639 (1980).
Swali, et al., "The stereospecific synthesis of 'orthogonally' protected lanthionines", Tetrahedron 58, p. 9101-9109 (2002).
Dugave, et al., "Synthesis of natural and non natural orthogonally protected lanthionines from N-tritylserine and allo-threonine derivatives", Tetrahedron: Asymmetry, vol. 8, No. 9, pp. 1453-1465 (1997).
Probert, et al., "Lanthionines for Solid Phase Synthesis", Tetrahedron Letters, vol. 37, No. 7, pp. 1101-1104 (1996).
Ösapay, et al., "Lanthionine-Somatostatin Analogs: Synthesis, Characterization, Biological Activity, and Enzymatic Stability Studies", J. Med. Chem. 40, p. 2241-2251 (1997).
Melacini, et al., "A Refined Model for the Somatostatin Pharmacophore: Conformational Analysis of Lanthionine—Sandostatin Analogs", J. Med. Chem. 40, p. 2252-2258 (1997).
Burrage, et al., "Biomimetic Synthesis of Lantibiotics", Chem. Eur. J. vol. 6, No. 8, p. 1455-1466 (2000).

(Continued)

*Primary Examiner*—Cecilia Tsang
*Assistant Examiner*—Julie Ha
(74) *Attorney, Agent, or Firm*—McDonnell Boehnen Hulbert & Berghoff LLP

(57) ABSTRACT

The present invention provides a method of synthesizing an intramolecularly bridged polypeptide comprising at least one intramolecular bridge. The present invention further provides a method of synthesizing an intramolecularly bridged polypeptide comprising two intramolecular bridges, wherein the two intramolecular bridges form two overlapping ring, two rings in series, or two embedded rings. The present invention also provides methods for synthesizing lantibiotics, including Nisin A. Additionally, the invention provides intramolecularly bridged polypeptides synthesized by the methods disclosed herein and differentially protected orthogonal lanthionines.

10 Claims, 4 Drawing Sheets

OTHER PUBLICATIONS

Galande, et al., "A facile method for the direct synthesis of lanthionine containing cyclic peptides", Letters in Peptide Science, 8, p. 247-251 (2002).

Galande, et al., "Understanding Base-Assisted Desulfurization using a Variety of Disulfide-Bridged Peptides", Biopolymers, vol. 71, p. 534-551 (2003).

Xie, et al., "Lacticin 481: In Vitro Reconstitution of Lantibiotic Synthetase Activity", Science, vol. 303, p. 679-681 (2004).

Kupke, et al., "Purification and characterization of EpiA, the peptide substrate for post-translational modifications involved in epidermin biosynthesis", FEMS Microbiology Letters, 112, p. 43-48 (1993).

Kupke, et al., "Post-translational modifications of lantibiotics", Antonie van Leeuwenhoek, 69:139-150 (1196).

Kuipers, et al., "Protein engineering of lantibiotics", Antonie van Leeuwenhoek, 69:161-170 (1996).

International Search Report for corresponding application PCT/US2006/031510 dated Jul. 9, 2007.

Bregant, et al., "Orthogonally Protected Lanthionines: Synthesis and Use for the Solid-Phase Synthesis of an Analogue of Nisin Ring C", J. Org. Chem. 2005, 70, 2430-2438.

Mustapa, et al., "Synthesis of a Cyclic Peptide Containing Norlanthionine: Effect of the Thioether Bridge on Peptide Conformation", J. Org. Chem. 2003, 68, 8193-8198.

Li, et al., "Synthesis, Conformational Analysis and Biological Activities of Lanthionine Analogs of a Cell Adhesion Modulator", J. Peptide Sci. 7:82-91 (2001).

Paul, et al., "Chemical and Enzymatic Synthesis of Lanthionines", Mini-Review in Organic Chemistry, 2005, 23-27.

Mustapa, et al., "Synthesis of Orthogonally Protected Lanthionines", J. Org. Chem. 2003, 68, 8185-8192.

Shao, et al., "A Facile Synthesis of Orthogonally Protected Stereoisomeric Lanthionines by Regioselective Ring Opening of Serine β-Lactone Derivatives", J. Org. Chem. 1995, 60, 2956-2957.

Zuberi, et al., "Synthesis of Asymmetric Cystines", Tetrahedron Letters 39 (1998) 7567-7570.

* cited by examiner

Nisin A

Synthetic Nisin A lanthionine; Lan

β-methyllanthionine; MeLan

S-[(Z)-2-Aminovinyl]-D-cysteine; AviCys

S-[(Z)-2-Aminovinyl]-2-methyl-D-cysteine; AviCys 2,3-didehydroalanine; Dha (Z)-2,3-didehydrobutyrine; Dhb hydroxypropionyl 2-oxobutyryl 2-oxopropionyl

DIFFERENTIALLY PROTECTED ORTHOGONAL LANTHIONINE TECHNOLOGY

CROSS REFERENCE TO RELATED APPLICATIONS

This application claims the benefit of U.S. Ser. No. 60/708,086, which was filed on Aug. 12, 2005, and U.S. Ser. No. 60/808,907, which was filed on May 26, 2006, both of which are incorporated herein by reference in their entirety.

BACKGROUND

The development of antibiotics revolutionized the practice of medicine in the second half of the $20^{th}$ century. Mortality due to infectious diseases decreased markedly during this period. Armstrong et al., (1999) *PAMA.* 281, 61-66. Since 1982, however, deaths stemming from infectious diseases have steadily climbed in parallel with the rise of antibiotic resistant pathogens. A wide variety of medically important bacteria are becoming increasingly resistant to antibiotics commonly used in the treatment of clinical infections. Thousands of reports and books have appeared in the literature during the past 20 years that document this phenomenon. Armstrong et al., (1999) *PAMA.* 281, 61-66; Dessen et al., (2001) *Curr. Drug Targets Infect. Disord.* 1, 11-16; Rapp (2000) *Surg Infect (Larchmt).* 1, 39-47; Benin & Dowell (2001) *Antibiotic resistance and implications for the appropriate use of antimicrobial agents*, Humana Press, Totowa, N.J.

While there is a need to teach more appropriate use of antibiotics, more importantly there is a need for new antibiotics. Vancomycin is considered to be the last line of defense against many serious bacterial infections. The finding of vancomycin resistance strains of pathogenic bacteria is alarming; it portends the rise of multidrug resistant pathogens that would be untreatable with currently available drugs. The fear is that we will, in effect, return to the pre-antibiotic era unless new antibiotics are developed soon.

There is a small, structurally novel class of antibiotics called lantibiotics (Class I bacteriocins) which can be divided into 5 subclasses based on differences in their chemistry and biosynthesis: Type A(I), Type A(II), Type B, Two-Component and those of unknown structures. This class of antibiotics has been known for decades but has not been extensively tested for their potential usefulness in treating infectious diseases even though many lantibiotics are known to be both potent and have a broad spectrum of activity, notably against gram positive species. The principal reason for this is the general difficulty of obtaining these molecules in sufficient, cost effective amounts to enable their testing and commercialization.

Nisin A (FIG. 1) provides a good example of a lantibiotic, and of the number and types of chemical complexities associated with lantibiotics. Lantibiotics are rich in the sulfur-containing amino acids, lanthionine (Lan, ala-5-ala) and, frequently, 3-methyl-lanthionine (MeLan, abu-5-ala). Lan consists of alanine residues that are connected via thioether bridges to create ring structures that are critical for bioactivity. Typically there are 3-5 such rings on a lantibiotic, and often many of the rings overlap with each other. Lan and MeLan are believed to invariably have the meso-stereochemistry. In addition to the Lan and MeLan residues, there may be other post-translationally modified amino acids (FIG. 2) found in lantibiotics, such as 2,3-didehydroalanine (Dha), 2,3 didehydrobutyrine (Dhb), unsaturated lanthionine derivatives such as S-amino vinyl-D-cysteine (AviCys) and S-amino-D-methylcysteine, as well as D-alanine, 2-oxopropionyl, 2-oxobutyryl, and hydroxypropionyl residues. As in the case of Nisin A, the ring structures made by Lan and MeLan may be overlapped (e.g., rings D and E), further adding to the complexity of the molecule.

Gram positive bacteria are responsible for biosynthesis of the known lantibiotics. They make the mature molecule using a series of sequential enzymatic steps that act on a ribosomally synthesized prepropeptide. The genes responsible for encoding the modifying enzymes are typically clustered on an 8-10 Kb DNA fragment that may reside on the chromosome, a plasmid, or as part of a transposon. In Type A(I) lantibiotics, all the serine and threonine residues in the ribosomally synthesized prepeptide encoded by the lanA gene are dehydrated by an enzyme encoded by the lanB gene and these dehydrated amino acids are involved in the formation of thioether linkages to a nearby cysteine residue that is situated more toward the carboxyl end of the molecule. This reaction is catalyzed by the protein expressed by the lanC gene. In the case of certain lantibiotics, such as epidermin and mutacin 1140, the C-terminal cysteine is decarboxylated by the enzyme expressed by the lanD gene and converted into an S-amino vinyl-D-cysteine. Following transport out of the cell by the product of the lanT gene, the leader sequence of the modified prepropeptide is then cleaved by an extracellular protease encoded by lanP to produce mature antibiotic. Ra et al., (1996) *Microbiology-Uk.* 142, 1281-1288; Kupke & Gotz (1996) *Antonie Van Leeuwenhoek International Journal of General and Molecular Microbiology.* 69, 139-150; Kuipers et al., (1996) *Antonie Van Leeuwenhoek International Journal of General and Molecular Microbiology.* 69, 161-169.

Attempts to study lantibiotics for their potential usefulness in therapeutic applications have been hindered by the difficulty of obtaining them in sufficient amounts or with sufficient purity. Of the 40 or so lantibiotics characterized to date (Chatterjee et al., (2005) *Chemical Reviews.* 105, 633 683) only the Type A(I) lantibiotic, Nisin A, produced by *Streptococcus lactis*, has been made in commercial quantities, and it has found wide application as a food preservative for the past 50 years. The long-term, widespread use of Nisin A without the development of significant resistance (DelvesBroughton et al., (1996) *Antonie Van Leeuwenhoek International Journal of General and Molecular Microbiology.* 69, 193-202) has provided a strong impetus to develop additional lantibiotics for various applications.

Large scale production of Nisin A is performed using a fermentation process that has been refined over the years. A purification protocol for Nisin A has recently been filed as a US patent (USPA 2004/0072333). The protocol utilized a cocktail of expensive proteases followed by column chromatography. However, there is no published, commercially viable procedure for the purification of Nisin A. This demonstrates the current interest in finding an adequate method of producing pure Nisin A and other lantibiotics for therapeutic applications.

Various potential options present themselves for large scale production of lantibiotics. From the standpoint of cost of materials, fermentation processes unarguably would be the best method. Current fermentation methods for many lantibiotics yield microgram per liter quantities, which is not sufficient for drug development.

Alternatively, in vitro production utilizing the lantibiotic modification machinery has been explored in Type A(I) lantibiotics. Kupke & Gotz (1996) *Antonie Van Leeuwenhoek International Journal of General and Molecular Microbiology.* 69, 39-150; Kuipers et al., (1996) *Antonie Van Leeuwen-* hoek *International Journal of General and Molecular Microbiology.* 69, 161-169. The enzymes responsible for post-translational modification of the lantibiotic prepropeptide are not active in cell-free lysates or as purified entities, with the exception of LanD. Kupke & Gotz (1996) *Antonie Van Leeuwenhoek International Journal of General and Molecular Microbiology.* 69, 139-150; 10; Kupke & Gotz (1997) *Journal of Biological Chemistry.* 272, 4759-4762; Kupke et al., (1992) *Journal of Bacteriology.* 174, 5354-5361; Kupke et al., (1993) *Fems Microbiology Letters.* 112, 43-48; Kupke et al., (1995) *Journal of Biological Chemistry.* 270, 11282-11289; Kupke et al., (1994) *Journal of Biological Chemistry.* 269, 5653-5659. In the case of Type A(II) lantibiotics, it has been recently reported in *Science*, that in vitro synthesis of lacticin 481 is possible. Molecules belonging to this group and Type B lantibiotics use only a single multiheaded enzyme, LanM, to accomplish the formation of the Dha, Dhb, Lan, and MeLan residues. Xie et al., (2004) *Science.* 303, 679-681. The report of lacticin 481 biosynthesis did not provide any detailed information regarding yield or purity, but their work was performed on the nanogram scale. The progress described in this report represents a small but significant step forward, and its widely acclaimed reception further points to the pressing need for the development of lantibiotics as therapeutic agents.

A third option for commercial scale production of lantibiotics using the lan gene cluster cloned into appropriate expression vector(s) and a non-sensitive host is unlikely due to the complexity of the system and the likely need for differentially regulating expression of the various genes involved. The lan gene cluster for gallidermin has been cloned into *Bacillus subtilis* in an attempt to improve production of this particular lantibiotic. However, this strategy did not result in greatly increased yields and will not be suitable for all lantibiotics since gene regulatory sites are known to vary from species to species. A related approach made use of an artificial gene for mutacin 1140 cloned into *Escherichia coli*. This artificial gene replaced the natural codons for the serine and threonine residues involved in thioether bridge formation with cysteine codons. This modified gene was cloned in pET32 and expressed in the Origami strain of *E. coli* to maximize disulfide linkages. Novel chemical methods were developed to extrude a single sulfur atom from the disulfide groups thereby converting them to thioethers. In general, this method proved feasible, but the yields obtained were low owing to the multiple permutations of disulfide bonds and the difficulty in separating out the active form from non-active isomers.

Critical to the bioactivity of Nisin A and other lantibiotics are the often overlapping ring structures, creating a difficult problem to overcome synthetically. In vitro synthetic methods have been widely investigated for the synthesis of various lanthionine containing bioactive peptides as well as lantibiotics. The challenge of synthesizing lantibiotics is arduous and, thus far, no comprehensive synthetic strategy has evolved. Several methods of synthesizing lanthionines have been reported in the literature. These include the in situ-based desulfurizations of cystine units in preassembled peptides using basic or nucleophilic conditions. Galande et al., (2003) *Biopolymers (Peptide Science)* 71, 543-551; Galande & Spatola (2001) *Letters in Peptide Science.* 8, 247-251. The methods of desulfurizations are yet to show any commercial viability due to lack of diastereoselectivity and poor yields. Biomimetic approaches have also been used where Dha residues are generated in a preformed peptide followed by a Michael addition to form the lanthionine ring. The preorganization of the peptide presumably leads to a diastereoselective Michael addition. Burage et al., (2000) *Chemistry A European Journal.* 6, 1455-1466. Peptide cyclization on oxime resin has also been employed wherein a linear peptide containing an orthogonally protected lanthionine is synthesized followed by cyclization and cleavage of the cyclic peptide product. Melacini et al., (1997), *J. Med. Chem.* 40, 2252-2258; Osapay et al., (1997) *Journal of Medicinal Chemistry.* 40, 2441-2251. These methods are promising but lack the ability to produce lantibiotics with overlapping thioether rings. This becomes particularly important when one takes into account that most of the known lantibiotics contain overlapping rings.

Conceptually, there are clear advantages to developing in vitro synthetic approaches, including modifications of solid phase peptide synthesis (SPPS) methods, relative to biologic and biomimetic approaches. First, the composition of the molecules is not limited to the normal set of physiological amino acids; it is possible to design amino acid analogs and incorporate them using well-established solid phase synthesis methods. Parallel synthesis can also be brought to bear, thereby dramatically increasing the number of substrate candidates. Because the approach is performed entirely in vitro, many of the concerns that arise from in vivo syntheses of bioactive molecules are eliminated. For example, degradation of products during fermentation would not be a concern, nor would the cytotoxic effects of the bioactive molecule on the producer microorganism be of concern.

In order to achieve the goal of in vitro synthesis, orthogonal lanthionines with potentially suitable protecting groups have been designed for SPPS using different approaches, such as the Michael addition of cysteine to preformed Dha. Probert et al., (1996) *Tetrahedron Letters.* 37, 1101-1104. This method led to a 1:1 mixture of diastereomers and, hence, was shown to have little commercial value. The ring opening of serine lactone with protected cysteines has also been reported but this led to a mixture of lanthionines and thioesters. The ring opening of aziridines has been investigated but was shown to produce regioisomeric mixtures due to opening of the aziridine at the α and β position. Dugave & Menez (1997) *Tetrahedron-Asymmetry.* 8, 1453-1465; Swali et al., (2002) *Tetrahedron.* 58, 9101-9109. More recent reports suggest that alkylating a suitably protected cysteine with a protected β-bromoalanine can result in the synthesis of lanthionines, but this method does not permit the construction of molecules with overlapping rings. Zhu (2003) *European Journal of Organic Chemistry.* 20, 4062-4072.

Because the Fmoc/Boc protected analogs that are commercially available for SPPS are not sufficient to solve the challenge of synthesizing lantibiotics and other conformationally constrained bioactive peptides, there exists a need in the art for the synthesis of peptides with intramolecular bridges that create internal ring structures, including multiple rings and overlapping ring structures. In particular, there exists a need for in vitro methods for synthesizing lantibiotics on a large scale.

SUMMARY OF THE INVENTION

Accordingly, the present invention provides a method of synthesizing an intramolecularly bridged polypeptide comprising at least one intramolecular bridge comprising:

a) coupling the free carboxy terminus of a differentially protected orthogonal intramolecular bridge of formula

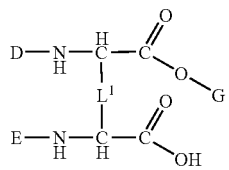

to a solid support or to the free amino terminus of an amino acid or polypeptide optionally bound to a solid support and wherein $L''$ represents covalently bound amino acid side chains, wherein D, E, and G are protecting groups, each of which is selectively removed under different reaction conditions, and wherein the reaction conditions for the removal of protecting group D are different from those for the removal of the amino protecting group of the amino acids of the remainder of the polypeptide chain;
  b) removing protecting group E to form a free amino terminus;
  c) adding an amino-protected amino acid to the free amino terminus and then deprotecting the amino acid to yield a new free amino terminus;
  d) optionally repeating c) one or more times;
  e) removing protecting group G to form a free carboxy terminus;
  f) coupling the free carboxy terminus of e) to the free amino terminus;
  g) removing protecting group D to form a free amino terminus; and
  h) optionally adding an amino-protected amino acid to the free amino terminus and then deprotecting the amino acid to yield a new free amino terminus; and
  i) optionally repeating h) one or more times.

The present invention further provides a method of synthesizing an intramolecularly bridged polypeptide comprising two overlapping intramolecular bridges comprising:
  a) covalently binding the free carboxy terminus of a first differentially protected orthogonal intramolecular bridge of formula

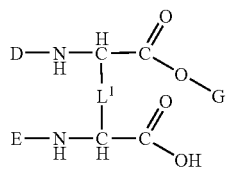

to a solid support or to the free amino terminus of an amino acid or polypeptide optionally bound to a solid support and wherein $L''$ represents covalently bound amino acid side chains, wherein D, E, and G are protecting groups, each of which is selectively removed under different reaction conditions, and wherein the reaction conditions for the removal of protecting group D are different from those for the removal of the amino protecting group of the amino acids of the remainder of the polypeptide chain;
  b) removing protecting group E to form a free amino terminus;
  c) adding an amino-protected amino acid to the free amino terminus and then deprotecting the amino acid to yield a new free amino terminus;
  d) optionally repeating c) one or more times;
  e) covalently binding the free carboxy terminus of a second differentially protected orthogonal intramolecular bridge of formula

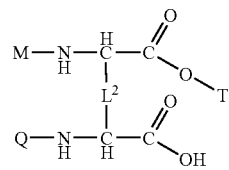

to the free amino terminus, wherein $L''$ is as defined above, wherein M, Q, and T are protecting groups, each of which is selectively removed under different reaction conditions, wherein D and M are removed only under different conditions, wherein G and T are removed only under different conditions, wherein the reaction conditions for the removal of protecting group M are different from those for the removal of the amino protecting group of the amino acids of the remainder of the polypeptide chain, and wherein E and Q are removed under conditions different from those that will remove D and those that will remove M;
  f) removing protecting group Q to form a free amino terminus;
  g) optionally adding an amino-protected amino acid to the free amino terminus and then deprotecting the amino acid to yield a new free amino terminus;
  h) optionally repeating g) one or more times;
  i) removing protecting group G of the first differentially protected orthogonal intramolecular bridge to form a free carboxy-terminus;
  j) coupling the free carboxy-terminus to the free amino terminus;
  k) removing protecting group D of the first differentially protected orthogonal intramolecular bridge to form a free amino terminus;
  l) optionally adding an amino-protected amino acid to the free amino terminus and then deprotecting the amino acid to yield a new free amino terminus;
  m) optionally repeating l) one or more times;
  n) removing protecting group T of the second differentially protected orthogonal intramolecular bridge forming a free carboxy-terminus;
  o) coupling the free carboxy-terminus to the free amino terminus;
  p) removing protecting group M of the second differentially protected orthogonal intramolecular bridge to form a free amino terminus; and
  q) optionally adding an amino-protected amino acid to the free amino terminus and then deprotecting the amino acid to yield a new free amino terminus; and
  r) optionally repeating q) one or more times.

Additionally, the present invention provides methods of synthesizing intramolecularly bridged polypeptides comprising two intramolecular bridges, wherein the two intramolecular bridges form two rings in series or two embedded rings as defined herein. The present invention further provides methods for synthesizing lantibiotics, including Nisin A.

In another aspect, the invention provides intramolecularly bridged polypeptides synthesized by the methods disclosed herein.

In a further aspect, the invention provides differentially protected orthogonal lanthionines of formula:

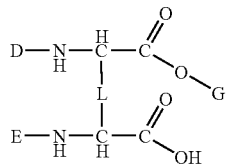

wherein D and E are different protecting groups and are, for example, Fmoc, Alloc, or IvDde, and G is a protecting group, for example propargyl ester or benzyl ester.

DETAILED DESCRIPTION OF THE INVENTION

Figure 1:
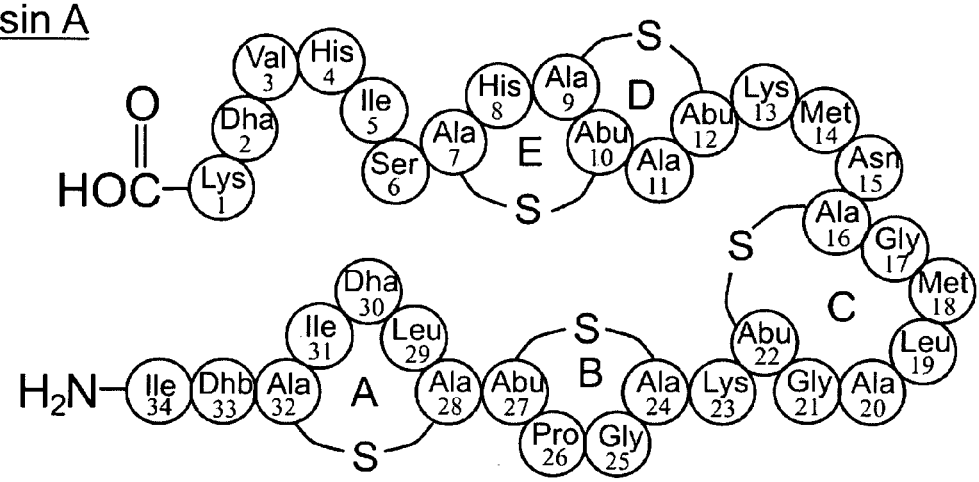
FIG. 1 shows the structure of Nisin A [SEQ ID NO:1], including intramolecular bridges between residues 7 and 10, creating ring E, between residues 9 and 12, creating ring D, between residues 16 and 22, creating ring C, between residues 24 and 27, creating ring B, and between residues 28 and 32, creating ring A. Rings A, B, and C exemplify ring structures in series, and rings D and E exemplify overlapping rings. Also shown is a synthetic Nisin A analog [SEQ ID NO:2].
Figure 1:
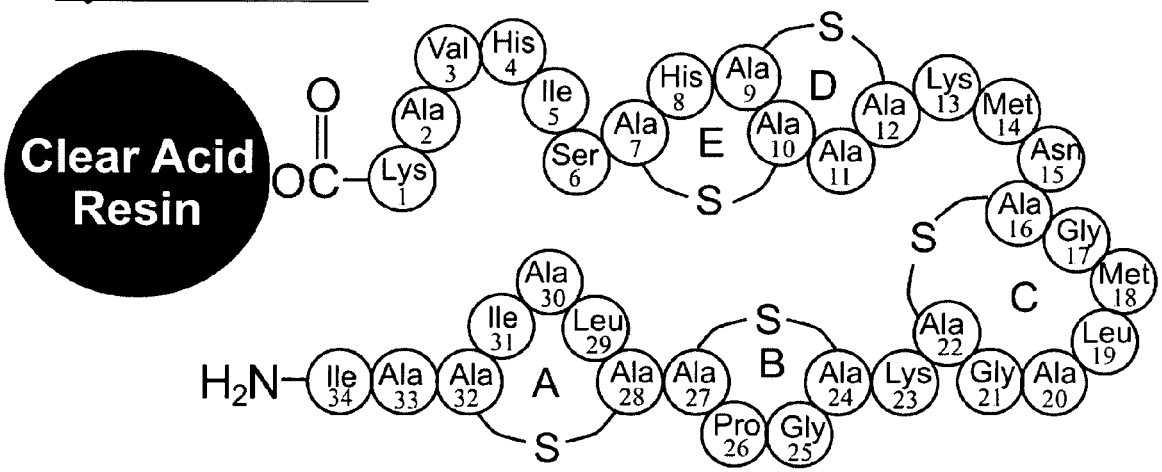

Differentially Protected Orthogonal Lanthionine Technology (DPOLT) for solid phase synthesis of peptides is disclosed herein. The technology depends on the bulk manufacture of various orthogonally protected peptide bridges whose active carboxyl and amino protecting groups can be differentially removed. The orthogonally protected peptide bridges can be used in, for example, solid phase peptide synthesis, to prepare conformationally constrained bioactive peptides containing intramolecular bridges forming ring structures. In particular, DPOLT can be used to synthesize polypeptides containing more than one intramolecular bridge and having overlapping ring structures.

While not so limited, DPOLT enables the in vitro production of structurally complex lantibiotics (including those with overlapping ring structures) to be made in a commercially viable fashion. The synthesis of lantibiotic peptides is performed using, for example, routine solid phase peptide synthesis methods incorporating into the peptide lanthionine analogs whose active carboxyl and amino groups are orthogonally protected with protecting groups that can be differentially removed. This method can provide a steady stream of novel antibiotics for, e.g., therapeutic applications.

Abbreviations

As used herein, the following abbreviations have the following meanings:
Alloc=allyloxycarbonyl
Boc=t-butoxycarbonyl
DMAP=dimethylaminopyridine
DMF=dimethylformamide
Fmoc=9-fluorenylmethoxy carbonyl
HMBC=Heteronuclear Multiple Bond Correlation
HMQC=Heteronuclear Multiple Quantum Correlation
HPLC=high performance liquid chromatography
ivDde=1-(4,4-dimethyl-2,6-dioxo-cyclohexylidene)-3-methyl-butyl
LC-MS=liquid chromatography-mass spectrometry
MS=mass spectrometry
NMR=nuclear magnetic resonance spectroscopy
NOESY=nuclear overhauser effect spectroscopy
TFA=trifluoroacetic acid
TLC=thin-layer chromatography
TOCSY=total correlation spectroscopy Intramolecularly Bridged Polypeptides The methods disclosed herein may be used to synthesize intramolecularly bridged polypeptides including, but not limited to, lantibiotics. As used herein, the terms "polypeptide", "protein" and "peptide" refer to polymers comprised of chains of amino acid monomers linked by amide bonds. Polypeptides may be formed by a condensation or coupling reaction between the α-carbon carboxyl group of one amino acid and the amino group of another amino acid. The terminal amino acid at one end of the chain (amino terminal) therefore has a free amino group, while the terminal amino acid at the other end of the chain (carboxy terminal) has a free carboxyl group. The intramolecularly bridged polypeptides of the invention may optionally be modified or protected with a variety of functional groups or protecting groups, including on the amino and/or carboxy terminus.

As used, herein, the terms "intramolecularly bridged peptide" or "intramolecularly bridged polypeptide" refer to a peptide chain having at least one intramolecular bridge. The terms "intramolecular bridge," "peptide bridge," "intramolecularly bridged moiety" or "bridge," as used herein, refer to the structure formed when two amino acid residues, contained within a single peptide chain, or prepared for incorporation into a single peptide chain, are covalently bound to each other through their side chains. Such a bond creates an internally crosslinked polypeptide. As used herein, the terms "ring" or "ring structure" refer to the crosslinked portion of the intramolecularly bridged polypeptide, i.e. the structure entailing the polypeptide chain between and including the two covalently bonded amino acid residues, along with the covalent bond formed by their side chains.

The intramolecularly bridged peptides of the invention have the general formula:

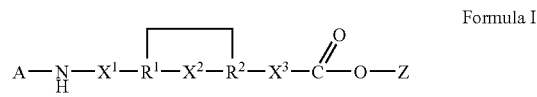

Formula I wherein A is either H or an amino terminus protecting group; Z is either H or a carboxy terminus protecting group; X" is a covalent bond, a single amino acid, or a peptide chain at least 2 amino acids in length; and R" is an amino acid residue forming an intramolecular bridge through its side chain. There may additionally be intramolecular bridges between side chains within a single "X" peptide chain or between amino acids situated in different "X" peptide chains.

As used herein, the terms "amino terminus protecting group" and "carboxy terminus protecting group" refer to any chemical moiety capable of addition to and optionally removal from a reactive site (an amino group and a carboxy group, respectively, in this instance) to allow manipulation of a chemical entity at sites other than the reactive site.

Figure 2:
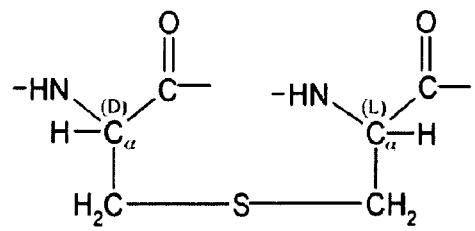
FIG. 2 shows non-limiting examples of post-translationally modified amino acids.
Figure 2:
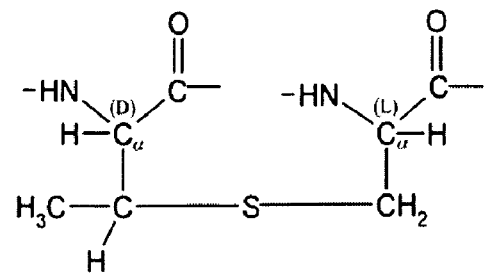
Figure 2:
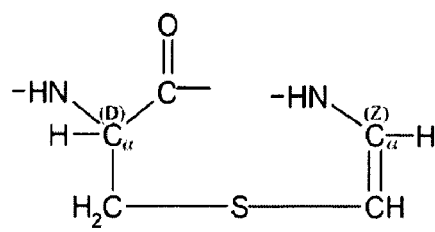
Figure 2:
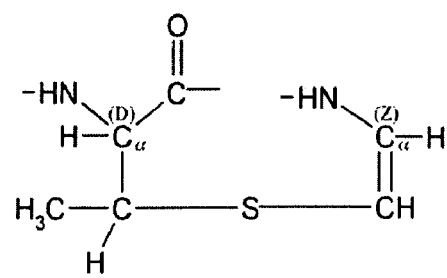
Figure 2:
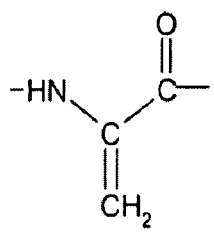
Figure 2:
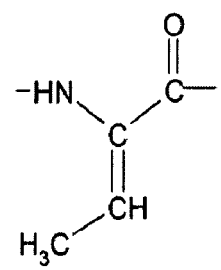
Figure 2:
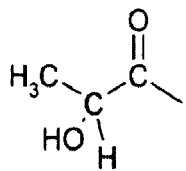
Figure 2:
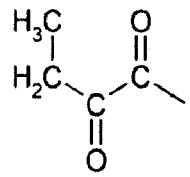
Figure 2:
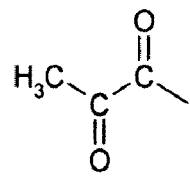

The amino acids of the intramolecularly bridged polypeptides of the invention may include the 20 amino acids that occur naturally as well as unnatural amino acids, amino acid analogs, and peptidomimetics. Spatola, (1983) in *Chemistry and Biochemistry of Amino Acids, Peptides, and Proteins*, Weinstein, ed., Marcel Dekker, New York, p. 267. All of the amino acids used in the present invention may be either the D- or L-optical isomers. In a preferred embodiment, the intramolecularly bridged polypeptides of the invention contain one or more of the following residues, in any combination: 2,3-didehydroalanine (Dha), (Z)-2,3-didehydrobutyrine (Dhb), hydroxypropionyl, 2-oxobutyryl, and 2-oxopropionyl (see FIG. 2).

It will be appreciated by one of ordinary skill in the art that the intramolecularly bridged peptides of the invention may have more than one intramolecular bridge, creating a wide range of possible structures. For example, for an intramolecularly bridged polypeptide containing two intramolecular bridges, the intramolecular bridges may be in series, embedded, or overlapping as shown below.

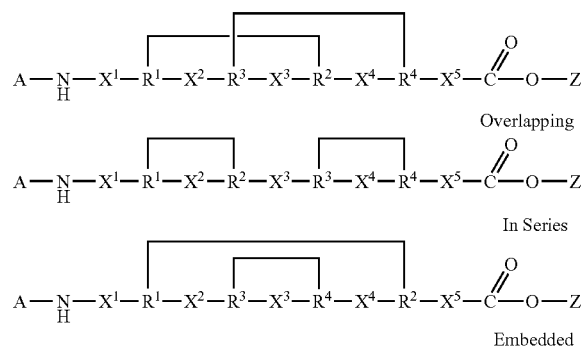

Overlapping

In Series

Embedded

Where two intramolecular bridges are overlapping, it is meant that one amino acid of the second intramolecular bridge is in between, in the primary amino acid sequence, the two amino acids of the first intramolecular bridge and the other amino acid of the second intramolecular bridge is either before both or after both amino acids of the first intramolecular bridge. Where two intramolecular bridges are in series, it is meant that both amino acids of the second intramolecular bridge are, in the primary amino acid sequence, before both or after both amino acids of the first intramolecular bridges. Where the two intramolecular bridges are embedded, it is meant that both amino acids of the second intramolecular bridge are between, in the primary amino acid sequence, the two amino acids of the first intramolecular bridge.

Where the intramolecularly bridged peptide has three or more intramolecular bridges, a greater number of possible structures may be formed. There may be multiple overlapping rings, for example. In a non-limiting example, an intramolecularly bridged polypeptide may have 5 intramolecular bridges, where 2 of the 5 bridges form overlapping ring structures and the remaining 3 bridges are in series with each other and with the overlapping rings. Lantibiotic Nisin A represents such a structure (see FIG. 1).

In a preferred embodiment, the intramolecularly bridged polypeptides of the invention are lantibiotic peptides. In a more preferred embodiment, the intramolecularly bridged polypeptides of the invention are Nisin A and analogs thereof.

Differentially Protected Orthogonal Intramolecular Bridges

The orthogonally protected intramolecular bridges according to the invention have the following general formula:

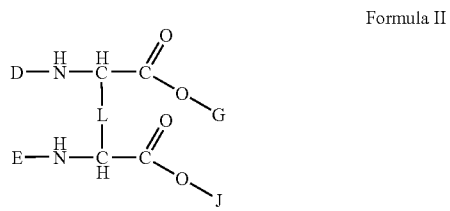

Formula II wherein L represents covalently bound amino acid side chains, D and E are hydrogen or an amino terminus protecting groups, and G and J are hydrogen or a carboxy terminus protecting group.

The bond comprising the amino acid side chains may be, but is not limited to, a thioether, a disulfide, an amide, or an ether. In a preferred embodiment, the intramolecular bridge comprises a thioether bond.

The incorporation of "differentially protected" or "orthogonally protected" intramolecular bridges in the synthesis of polypeptide provides for the selective removal of their protecting groups separate and apart from the removal of protecting groups on other portions of the peptide chain, including other intramolecular bridges. In other words, the protecting groups of a particular intramolecular bridge are selected such that their cleavage conditions do not compromise the stability of other protecting or functional groups on the polypeptide. The cross reactivity during deprotection of these groups is minimal and can be monitored by standard mass spectroscopy techniques. The desired product can be purified away from these impurities by standard HPLC or other techniques. Cleavages can be affected in any selected order of priority.

Protecting groups, and the manner in which they are introduced and removed are described, for example, in "Protective Groups in Organic Chemistry," Plenum Press, London, N.Y. 1973; and in "Methoden der organischen Chemie," Houben-Weyl, 4th edition, Vol. 15/1, Georg-Thieme-Verlag, Stuttgart 1974; and in Theodora W. Greene, "Protective Groups in Organic Synthesis," John Wiley & Sons, New York 1981. A characteristic of many protecting groups is that they can be removed readily, i.e., without the occurrence of undesired secondary reactions, for example by solvolysis, reduction, photolysis, by the use of organometallic catalysis such as organopalladium and organocobalt catalysts, or alternatively under physiological conditions.

Numerous protecting groups are known in the art. An illustrative, non-limiting list of protecting groups includes methyl, formyl, ethyl, acetyl, t-butyl, anisyl, benzyl, trifluoroacetyl, N-hydroxysuccinimide, t-butoxycarbonyl, benzoyl, 4-methylbenzyl, thioanizyl, thiocresyl, benzyloxymethyl, 4-nitrophenyl, benzyloxycarbonyl, 2-nitrobenzoyl, 2-nitrophenylsulphenyl, 4-toluenesulphonyl, pentafluorophenyl, diphenylmethyl, 2-chlorobenzyloxycarbonyl, 2,4,5-trichlorophenyl, 2-bromobenzyloxycarbonyl, 9-fluorenylmethyloxycarbonyl, triphenylmethyl, and 2,2,5,7,8-pentamethylchroman-6-sulphonyl. For discussions of various different types of amino- and carboxy-protecting groups, see, for example, U.S. Pat. No. 5,221,736 (issued Jun. 22, 1993); U.S. Pat. No. 5,256,549 (issued Oct. 26, 1993); U.S. Pat. No. 5,049,656 (issued Sep. 17, 1991); and U.S. Pat. No. 5,521,184 (issued May 28, 1996).

Any combination of protecting groups may be used, provided the protecting groups can be selectively removed during synthesis of the target intramolecularly bridged polypeptide. In a preferred embodiment, the amino terminal protecting groups are selected from the group consisting of Fmoc, Alloc, and IvDde. In another preferred embodiment, the carboxy terminal protecting groups are selected from the group consisting of propargyl ester and benzyl ester.

In a preferred embodiment, the orthogonally protected intramolecular bridge is an orthogonally protected lanthionine or lanthionine derivative. In a more preferred embodiment, the orthogonally protected intramolecular bridge is amino-terminally and/or carboxy-terminally protected lanthionine (Lan), β-methyllanthionine (MeLan), S-[(Z)-2-Aminovinyl]-D-cysteine (AviCys), or S-[(Z)-2-Aminovinyl]-2-methyl-D-cysteine (see FIG. 2). Such orthogonally protected intramolecular bridges can be synthesized by methods known in the art.

Figure 3:
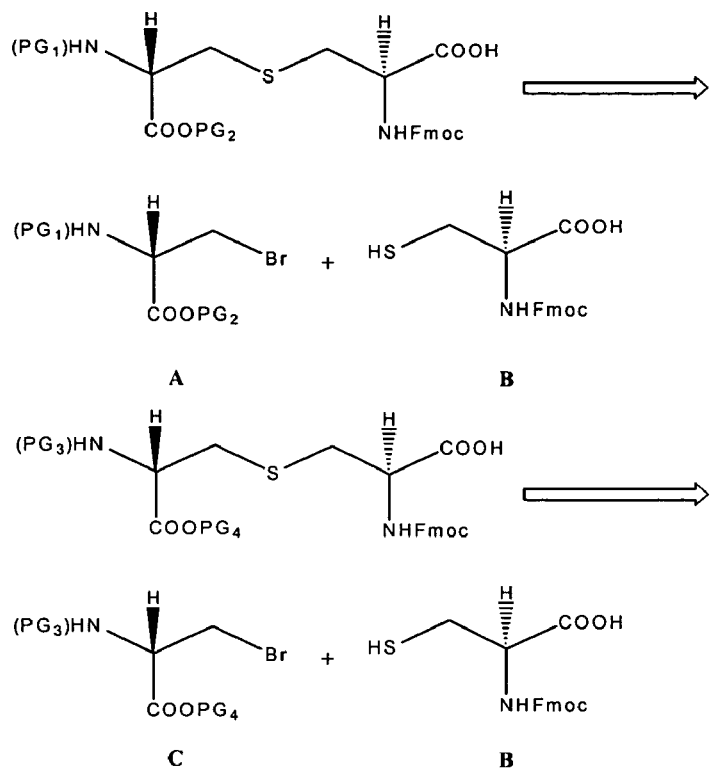
FIG. 3 shows a retrosynthetic strategy for making differentially protected lanthionines.

In a more preferred embodiment, the intramolecular bridge is lanthionine. Protected lanthionines can be synthesized as shown retrosynthetically in FIG. 3, using routine methodology. Stereochemistry of the lanthionine products can be assured at this stage by beginning with the correct stereoisomers of the appropriate amino acids, for example cysteine and serine.

In a more preferred embodiment, the intramolecular bridge is either Lanthionine 1 or Lanthionine 2:

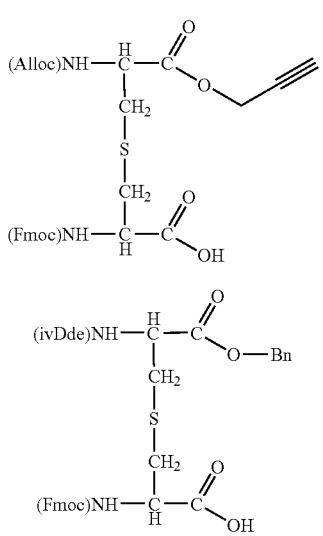

Lanthionine 1

Figure 5:
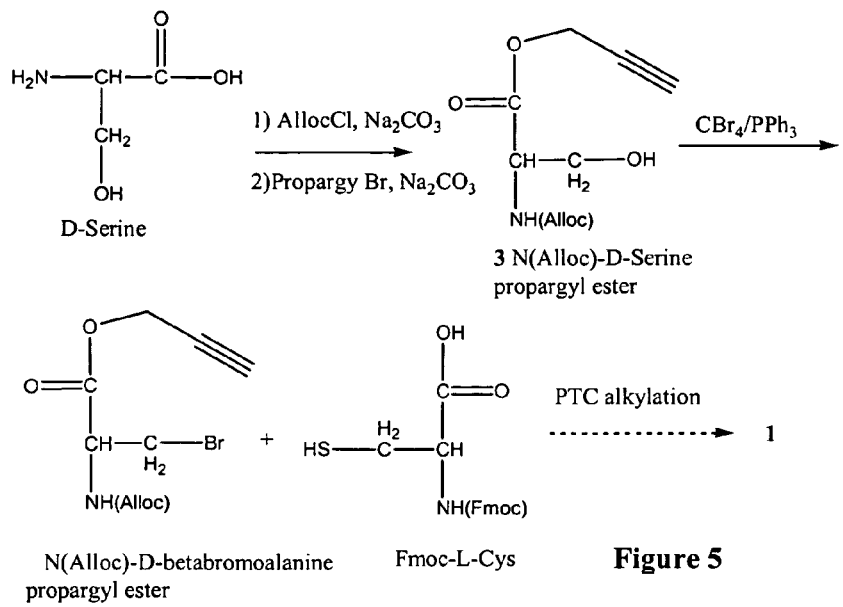
FIG. 5 shows the synthetic strategy for a orthogonally protected Lanthionine 1, including the synthesis of N(Alloc)-D-β-Bromoalanine Propargyl ester.
Figure 6:
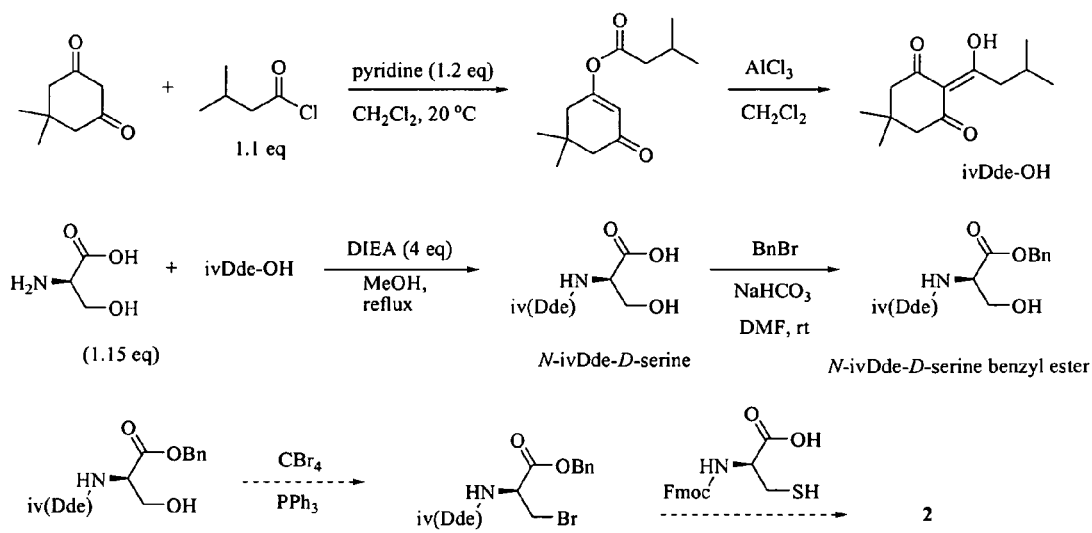
FIG. 6 shows the synthetic strategy for a orthogonally protected Lanthionine 2, including the synthesis of N(ivdDe)-D-β-Bromoalanine Benzyl ester.

Lanthionine 2 which may be synthesized, for example, as outlined in FIGS. 5 and 6, respectively. Briefly, referring to FIG. 5, for Lanthionine 1, D-serine is converted to its amino terminally protected Alloc derivative and subsequently converted to the carboxy terminally protected propargyl ester. N(Alloc)-D-Serine propargyl ester is converted to its corresponding β-bromoalanine derivative. The conversion may be achieved, for example, by dissolving N(Alloc)-D-Serine propargyl ester in dichloromethane and treating the solution with one equivalent of carbon tetrabromide and triphenylphosphine. These reactions are very mild and have been routinely used to convert hydroxyls to bromides. Zhu (2003) *European Journal of Organic Chemistry*. 20, 4062-4072. Alternatively, the syntheses are achieved using phosphorous tribromide in a solvent such as toluene or dichloromethane followed by mild basic workup to afford the desired D-β-bromoalanines. Olah et. al. (1980) *Journal of Organic Chemistry*. 45, 1638-1639. Other methods may also be utilized. Finally, the β-bromoalanine derivative is reacted with Fmoc-L-Cys under suitable alkylation conditions to form Lanthionine 1. Lanthionine 2 can be similarly synthesized as outlined in FIG. 6.

Synthesis of Intramolecularly Bridged Polypeptides

The intramolecularly bridged polypeptides of the invention can be synthesized by any means providing for the use and incorporation of orthogonally protected intramolecular bridges, including, but not limited to, solid phase peptide synthesis (SPPS), solution phase peptide synthesis, native chemical ligation, intein-mediated protein ligation, and chemical ligation, or a combination thereof. In a preferred embodiment, the intramolecularly bridge polypeptides of the invention are synthesized using a modified version of standard SPPS. The intramolecularly bridged polypeptides of the invention may be synthesized by either manual SPPS or by using commercially available automated SPPS synthesizers.

SPPS has been known in the art since the early 1960's (Merrifield, R. B., *J. Am. Chem. Soc.*, 85:2149-2154, 1963), and is widely employed. There are several known variations on the general approach. (See, for example, "Peptide Synthesis, Structures, and Applications" @ 1995 by Academic Press, Chapter 3 and White (2003) *Fmoc Solid Phase Peptide Synthesis, A practical Approach*, Oxford University Press, Oxford). Very briefly, in solid phase peptide synthesis, the desired C-terminal amino acid residue is coupled to a solid support. The subsequent amino acid to be added to the peptide chain is protected on its amino terminus with Boc, Fmoc, or another suitable protecting group, and its carboxy terminus is activated with a standard coupling reagent. The free amino terminus of the support-bound amino acid is allowed to react with the subsequent amino acid, coupling the two amino acids. The amino terminus of the growing peptide chain is deprotected, and the process is repeated until the desired polypeptide is completed.

In accordance with the methods of the invention, intramolecularly bridged peptides may be synthesized by incorporating differentially protected orthogonal intramolecular bridges into standard SPPS. The portions of the polypeptide chain that are not part of the intramolecular bridge may be synthesized by standard SPPS techniques known in the art. In a preferred embodiment, amino terminally Fmoc- or Boc- protected amino acids are utilized. In a more preferred embodiment, Fmoc-based SPPS is used. The differentially protected orthogonal intramolecular bridges are incorporated into the polypeptide chain through selective deprotection of its active amino and carboxy groups.

The methods of the invention may be used to synthesize an intramolecularly bridged polypeptide having a single intramolecular bridge as shown in general Formula III:

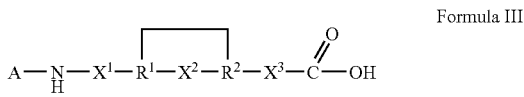

Formula III wherein A, X″, and R″ are as previously defined for Formula I. Such a polypeptide is prepared using a single intramolecular bridge of general formula IV:

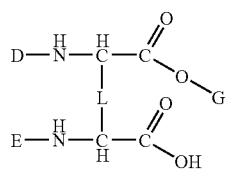

Formula IV wherein L represents covalently bound amino acid side chains, D and E are amino terminus protecting groups, and G is a carboxy terminus protecting group.

Briefly, the intramolecular bridge is coupled through its free carboxy terminus to a peptide chain attached to a solid support, or directly to the solid support. Additional amino acids are coupled to the free amino terminus of the intramolecular bridge following its deprotection (removal of E). The protecting group (G) on the remaining carboxy group of the intramolecular bridge is removed and the carboxy group is coupled to the free amino terminus of the polypeptide chain so formed. Additional amino acids may optionally be subsequently added to the remaining amino group.

During the synthesis of the polypeptides of the invention, at any one time the there will be a only single "free amino terminus" on the growing polypeptide chain and a single "free carboxy terminus" to be coupled to the free amino terminus. Each time an amino acid is added and deprotected the free amino terminus will be blocked by the added amino acid and, if the newly added amino acid is subsequently deprotected, a new free amino terminus will be formed. One skilled in the art will understand that under such circumstances there is only a single free amino terminus.

More specifically, in the synthesis of an intramolecularly bridged polypeptide having a single intramolecular bridge, D is selected so that the reaction conditions for the removal of protecting group D do not result in the removal of E or G and/or of the amino protecting group of the amino acids of the remainder of the polypeptide chain. The converse applies as well. In other words, as a non-limiting example, if the polypeptide is synthesized using Fmoc-based SPPS, D is selected so that it can be selectively cleaved under conditions that do not remove E, G, and/or Fmoc. Similarly, D and G are selected so that the conditions for the removal of Fmoc do not result in the cleavage of D or G. In a preferred embodiment, amino protecting group E is equivalent to the amino protecting group of the amino acids of the polypeptide chain that are not part of the intramolecular bridge. Therefore, where, for example, Fmoc-based SPPS is used, E is preferably Fmoc.

Synthesis of the intramolecularly bridged polypeptide begins with the coupling of the C-terminal amino acid to a solid support. The term "solid support" refers to any solid phase material upon which a polypeptide is synthesized. Solid support encompasses terms such as "resin", "solid phase", and "support". A solid support may be composed of organic polymers such as polystyrene, polyethylene, polypropylene, polyfluoroethylene, polyethyleneoxy, and polyacrylamide, as well as co-polymers and grafts thereof. A solid support may also be inorganic, such as glass, silica, controlled-pore-glass (CPG), or reverse-phase silica with suitable groups on which the amino acids can be attached and cleaved in a facile manner. The configuration of a solid support may be in the form of beads, spheres, particles, granules, or a surface. Surfaces may be planar, substantially planar, or non-planar. Solid supports may be porous or non-porous, and may have swelling or non-swelling characteristics. A solid support may be configured in the form of a well, depression or other vessel. A plurality of solid supports may be configured in an array, addressable for robotic delivery of reagents, or by detection means including scanning by laser illumination and confocal or deflective light gathering. Many solid supports are commercially available. The coupling of the first amino acid to the solid support may be monitored for completion by assays known in the art.

In a preferred embodiment, Fmoc amino acids are used in the synthesis of the polypeptide chain. Fmoc amino acids are commercially available or can be synthesized by methods known in the art. Additional amino acids may be added to the polypeptide chain using standard SPPS methodology. Where, for example, Fmoc amino acids are used, the Fmoc amino protecting group of the C-terminal amino acid, once coupled to the resin, can be removed by, for example, exposure to 20% piperidine in DMF. The next Fmoc amino acid may be coupled to the polypeptide chain using standard coupling chemistry. Amino acids having reactive side chains may be protected with suitable protecting groups so their side chains remain protected throughout the synthesis of the intramolecularly bridged polypeptide of interest. The steps of coupling and deprotection may be repeated as desired using the appropriate amino acids. This completes the synthesis of $X^3$ of general formula III.

The intramolecular bridge is coupled to the growing polypeptide chain through standard coupling chemistry. Alternatively, if the intramolecular bridge falls at the C-terminal end of the intramolecularly bridged polypeptide, the intramolecular bridge may be coupled directly to the resin through its free carboxy group. Protecting group E is then selectively removed under appropriate conditions, for example using 20% piperidine in DMF where E is Fmoc. Referring to general formula III, $R^2$ is now coupled to the polypeptide chain. One or more amino acids may be subsequently added to the polypeptide chain through sequential coupling and deprotection ($X^2$ of general formula III).

Next, protecting group G is selectively removed under appropriate conditions. In a preferred embodiment, G is either a propargyl group, which may be cleaved using dicobalt-octacarbonyl in dichloromethane, or benzyl ester, which may be cleaved using a hydrogenation protocol that uses palladium on charcoal and cyclohexadiene in dichloromethane. This completes the addition of $R^1$ of general formula III, whereby the intramolecular bridge is completely incorporated into the polypeptide, forming the ring structure.

Protecting group D may then be selectively deprotected under appropriate conditions. In a preferred embodiment, D is either Alloc, which may be cleaved using 20 mol % Pd(PPh$_3$)$_4$ and 20-25 equivalents PhSiH$_3$ in dichloromethane, or ivDde, which can be cleaved by 2-10% hydrazine in DMF. The intramolecularly bridged polypeptide may be subsequently lengthened through sequential coupling and deprotection of additional amino acids ($X^1$ in general formula III).

Intramolecularly bridged polypeptides with multiple rings in series, i.e. having more than one intramolecular bridge, may be similarly synthesized using a single differentially protected intramolecular bridge. Optionally, more than one differentially protected intramolecular bridge, differing from each other only by their protecting groups, may be used to synthesize a polypeptide having multiple rings. Multiple differentially protected intramolecular bridges, varying in their side chain structure (e.g. Lan and MeLan), may also be used to incorporate different intramolecularly bridged moieties. The protecting groups on such subsequent bridges may be the same or different than the protecting groups on the first intramolecular bridge incorporated into the polypeptide chain. The intramolecularly bridged polypeptide with multiple rings in series is synthesized by completely incorporating a first intramolecular bridge into the polypeptide chain, forming the first ring structure, removing the terminal amino protecting group, optionally extending the polypeptide chain through sequential coupling and deprotection of additional amino acids, completely incorporating a second intramolecular bridge (same or different than the first intramolecular bridge) through its carboxy terminus, optionally extending the polypeptide, and repeating these steps as desired to synthesize the target intramolecularly bridge polypeptide.

For intramolecularly bridged polypeptides with multiple rings that either overlap or are embedded, more than one orthogonally protected intramolecular bridge must be used. While the side chain structures of the multiple orthogonally protected intramolecular bridges may be the same or different, the protecting groups must be differentially orthogonally protected to permit the selective deprotection of their respective amino and carboxy groups. The number of such bridges depends on the number of overlapping or embedded rings. Where, for example, two rings of the intramolecularly bridged polypeptide overlap each other, or one is embedded within the other, two different differentially protected orthogonal intramolecular bridges are used; where, for example, 3 rings overlap each other, or are embedded within each other, three different differentially protected orthogonal intramolecular bridges are used, etc.

In a non-limiting example, where the intramolecularly bridged polypeptide of interest contains two overlapping rings, two differentially protected orthogonal intramolecular bridges of the general formulas V and VI are used:

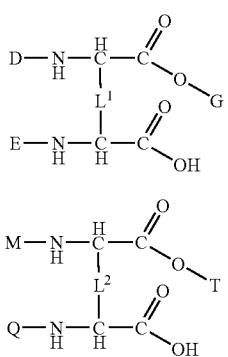

Formula V

Formula VI wherein $L^1$ and $L^2$ represent covalently bound amino acid side chains ($L^1$ may be the same or different than $L^2$), D, M, E, and Q are amino terminus protecting groups, and G and T are carboxy terminus protecting groups; wherein D and M are cleavable only under different conditions; wherein E and Q may be cleaved under the same conditions; wherein E and Q are cleaved under conditions different from those that will cleave D and those that will cleave M; and wherein G and T are cleavable only under different conditions. In a preferred embodiment, amino protecting groups E and Q are equivalent to the amino protecting group of the amino acids of the polypeptide chain that are not part of the intramolecular bridge. Therefore, where, for example, Fmoc-based SPPS is used, E and Q are preferably Fmoc, but are not so limited. In such a situation, E and Q may also be, for example, Boc.

According to the methods of the invention, an intramolecularly bridged polypeptide containing two overlapping rings may be synthesized by first coupling of the C-terminal amino acid to a solid support. Additional amino acids may be optionally added to the polypeptide chain using standard SPPS methodology. In a preferred embodiment, Fmoc amino acids are used in the synthesis of the polypeptide chain. Amino acids having reactive side chains may be protected with suitable protecting groups so their side chains remain protected throughout the synthesis of the intramolecularly bridged polypeptide of interest. The steps of coupling and deprotection may be repeated as desired using the appropriate amino acids. The intramolecular bridge of general formula V is then coupled to the growing peptide chain through its free carboxy group, and E is subsequently cleaved. D and G remain unaffected. In a preferred embodiment, E is Fmoc. One or more amino acids may then optionally be sequentially coupled to the free amino terminus of the polypeptide by cycling through coupling and deprotection steps in accordance with standard SPPS. Next, the intramolecular bridge of general formula VI is coupled to the growing peptide chain through its free carboxy group, and Q is subsequently cleaved. D, G, M, and T remain unaffected. In a preferred embodiment, Q is Fmoc. Again, one or more amino acids may then optionally be sequentially coupled to the free amino terminus of the polypeptide. To form the first ring, G is then cleaved using appropriate deprotection chemistry and the resulting free carboxy group is coupled to the free amino terminus of the polypeptide chain. Protecting groups D, M, and T remain unaffected. Subsequently, protecting group D is removed under suitable conditions, exposing a free amino group. Protecting groups M and T remain unaffected during the cleavage of D. Additional amino acids may then optionally be coupled to the free amino group at the N-terminus of the polypeptide. To form the second ring, and thus the overlapping rings, T is cleaved under suitable conditions and the resulting free carboxy group is coupled to the free amino terminus of the polypeptide chain. Protecting group M may then be cleaved under appropriate conditions, and the polypeptide chain further extended through the sequential coupling of additional amino acids.

According to the methods of the invention, an intramolecularly bridged polypeptide containing two embedded rings may be similarly synthesized using two differentially protected orthogonal intramolecular bridges of general formulas V and VI. The synthesis of intramolecularly bridged polypeptide containing two embedded rings is comparable to the synthesis of an intramolecularly bridged polypeptide containing two overlapping rings, differing only in the order of deprotection and coupling of the intramolecular bridges of formulas V and VI. Specifically, the intramolecular bridge of formula V is coupled to the free amino terminus of a peptide chain linked through its carboxy terminus to a solid support, or the intramolecular bridge of formula V is coupled directly to the solid support. E is subsequently cleaved, and one or more amino acids may then optionally be sequentially coupled to the free amino terminus of the polypeptide by cycling through coupling and deprotection steps in accordance with standard SPPS. Next, the intramolecular bridge of general formula VI is coupled to the growing peptide chain through its free carboxy group, and Q is subsequently cleaved. Again, one or more amino acids may then optionally be sequentially coupled to the free amino terminus of the polypeptide. To form the first ring, T is then cleaved using appropriate deprotection chemistry and the resulting free carboxy group is coupled to the free amino terminus of the polypeptide chain. Subsequently, protecting group M is removed under suitable conditions, exposing a free amino group. Additional amino acids may then optionally be coupled to the free amino group at the N-terminus of the polypeptide. To form the second ring, and thus the embedded rings, G is cleaved under suitable conditions and the resulting free carboxy group is coupled to the free amino terminus of the polypeptide chain. Protecting group D may then be cleaved under appropriate conditions, and the polypeptide chain further extended through the sequential coupling of additional amino acids.

One of skill in the art will appreciate that more complex molecules may be similarly prepared through variations of the above methods. For example, a polypeptide having two overlapping rings, and 3 additional rings in series may be synthesized by combining the methods disclosed for the synthesis of intramolecularly bridged polypeptides containing overlapping rings with the methods disclosed for the synthesis of intramolecularly bridged polypeptides having rings in series.

During synthesis of an intramolecularly bridged polypeptide, the progress and accuracy of the synthesis may optionally be monitored by various techniques known in the art, including, but not limited to, Maldi and LC-MS. Upon completion of the synthesis, the intramolecularly bridged polypeptide is cleaved from the solid support under suitable conditions. Where the synthesized polypeptide contains significant amounts of sulfur (e.g., for lanthionine containing polypeptides), a TFA/thioanisole/water/phenol/ethanedithiol (82.5/5/5/5/2.5) cocktail may be used. Progress of the cleavage reaction may be monitored periodically by LC-MS or another suitable technique. Dependent on the side chain protecting groups selected, their cleavage may be effected during cleavage of the polypeptide from the resin, or alternatively in a separate step. The final product may be isolated by, for example, precipitation from cold ether, and purified by known methods including, but not limited to, reverse phase HPLC.

The intramolecularly bridged polypeptides of the invention may be analyzed structurally and for biochemical function by known techniques. Structural analysis may be achieved by techniques including, but not limited to, 2-dimensional NMR and X-ray crystallography. Intramolecularly bridged polypeptides have been successfully analyzed structurally using 2-dimensional NMR TOCSY acquired at 60 ms mixing time (Braunschweiler & Ernst (1983), *Journal of Magnetic Resonance* 53, 521-528) and NOESY acquired at 200 ms, 400 ms, 450 ms. Kumar et. al. (1980), *Biochem. Biophys. Res. Commun.* 95, 1-6. Smith, J. L. (2002) *Dissertation*, University of Florida, Gainesville. Smith et. al. (2000), *European Journal of Biochemistry* 267, 6810-6816.

In a preferred embodiment, the methods of the invention are used to synthesize intramolecularly bridged polypeptides containing one or more lanthionine or lanthionine derivative(s). In a more preferred embodiment, the methods of the invention are used to synthesize lantibiotics. In a more preferred embodiment, the methods of the invention are used to synthesize Nisin A and analogs thereof.

Nisin A and analogs thereof can be assayed for biological activity using known methods. (Hillman et. al. (1984), *Infection and Immunity* 44, 141-144; Hillman et. al. (1998), *Infection and Immunity* 66, 2743-2749). The structural analysis Nisin A and analogs thereof synthesized by the methods of the invention may be aided by comparison to the three dimensional structure of biologically produced Nisin A, previously determined by Van De Yen et al. by NMR (1991, *European Journal of Biochemistry* 202, 1181-1188). From the amino acid assignments made from this earlier covalent structure determination work, it is possible to quickly characterize the covalent linkages and identify all the relevant long range NOEs for the structural determination of Nisin A and analogs thereof synthesized by the methods of the invention.

Applications of DPOLT Technology

DPOLT is a platform technology that arose from a multidisciplinary approach. There are several advantages that make this technology so desirable. First and foremost, it will enable quick synthesis and screening of a substantial number of candidate lantibiotics and other bioactive peptides for their potential application in the realm of therapeutics without having to devote large amounts of time and expense to devising fermentation and purification methods for their analysis. There are approximately 50 lantibiotics containing overlapping thioether bridges, with more being discovered each year, that may be synthesized by the methods disclosed herein. These lantibiotics include Type A(I) lantibiotics Nisin A, Nisin Z, Subtilin, Ericin S, Ericin A, Streptin, Epidermin, [Val1-Leu6]-epidermin, Gallidermin, Mutacin 1140, Mutacin B-Ny266, Mutacin III, Mutacin I, Pep5, Epilancin K7, and Epicidin 280; Type A(II) lantibiotics Lacticin 481, Variacin, Mutacin II, StreptococcinA-FF22, Salivaricin A, [Lys2-Phe7]-salivaricin A, Plantaricin C, Sublancin 168, and Butyrivibriocin OR79A; Type B lantibiotics Cinnamycin, Duramycin, Duramycin B, Duramycin C, Curamycin C, Ancovenin, Mersacidin, Actagardine, Ala(0)-actagardine, and Subtilocin A; Two-Component lantibiotics Lacticin 3147A1, Lacticin 3147A2, Staphylococcin C55α; Staphylococcin C55β, Plantaricin Wα, Plantaricin Wβ, Cytolysin $L_L$, Cytolysin $L_S$; and other lantibiotics such as Ruminococcin A, Carnocin UI 49, Macedocin, Bovicin HJ50, Nukacin ISK-1, and SapB morphogen. (See, e.g., Chatterjee et al., 2005. *Chem. Rev.* 105, 633-83.)

From past experience, it seems likely that many fermentation and purification methods for many lantibiotics will not be quickly achieved. Nisin A, which was discovered over 50 years ago, remains the subject of intense study in order to find a quick and suitable method of purification for its development as a therapeutic agent. A recent U.S. patent application (US Patent Application 2004/0072333) attempts to achieve this end, but uses a variety of costly proteases and multiple purification steps. It is extremely likely that the SPPS methods employed by DPOLT will achieve the desired end in a much more cost efficient manner. Currently, over 35 bioactive molecules are commercially sold that are synthesized using SPPS methods, such as oxytocin, sandostatin and fuzeon, and, over time the demand will certainly increase. The use of DPOLT allows the site specific substitution of amino acids and their analogs, even in a combinatorial library approach, which provides an optimal method for finding new and improved therapeutic agents for their intended purpose. In this regard, DPOLT is the only existing technology for the synthesis of molecules with overlapping rings, and has the potential to make a variety of bioactive molecules, besides lantibiotics, for use in various applications. DPOLT enables in vitro production, e.g., of structurally complex lantibiotics (including those with overlapping, ring structures) to be made in a commercially viable fashion using routine solid phase peptide synthesis methods.

DPOLT provides two significant advantages in the screening and development of new lantibiotics for commercial applications: fermentation approaches are clearly preferable from the standpoint of cost of materials for production, but the time and effort required to optimize such methods may be prohibitive during the initial stages of drug discovery. In addition, as in the case of Nisin A, purification of high yield fermentations may not be readily achieved. Purification of the final product, typically, is not a significant problem in SPPS. DPOLT has the advantage of allowing screening of a large number of potentially useful compounds in a rapid fashion for clinical testing. For compounds that look promising, DPOLT provides a fast path to market, and also indicates those molecules that could be served by providing the necessary time and effort to develop fermentation methods. For compounds that lack the necessary characteristics for further development, such as those with poor spectrum of activity, flawed pharmacokinetics, toxicity problems, etc., DPOLT will allow the quick and efficient elimination of these from consideration. Finally, since DPOLT depends on solid phase peptide synthesis, it will be simple to screen and develop analogs with improved characteristics, such as those that overcome bacterial resistance. Thus, the method can be applied to other lantibiotics and peptides of interest and to identify ones that have functionally desirable and economically favorable characteristics.

The most obvious uses for DPOLT and the lantibiotics synthesized by the methods of the invention are the medical and veterinary treatment of bacterial infections. There are several other potential applications also. Lantibiotics are a well-established and attractive alternative to other bactericidal agents for use in food preservation and in cosmetics. DelvesBroughton et al., (1996) *Antonie Van Leeuwenhoek International Journal of General and Molecular Microbiology.* 69, 193-202; Rollema et al., (1995) *Applied and Environmental Microbiology.* 61, 2873-2878; Liu & Hansen, (1990) *Applied and Environmental Microbiology.* 56, 2551-2558; Huot et al., (1996) *Letters in Applied Microbiology.* 22, 76-79; Delvesbroughton, (1990) *Food Technology.* 44, 100; Delvesbroughton (1990) *Journal of the Society of Dairy Technology.* 43, 73-76; Delvesbroughton et al., (1992) *Letters in Applied Microbiology.* 15, 133-136; Thomas & Wimpenny (1996) *Applied and Environmental Microbiology.* 62, 2006-2012; Sahl & Bierbaum (1998) *Annual Review of Microbiology.* 52, 41-79. Additionally, lantibiotics have been studied with some success as topical disinfectants, particularly as mouthrinses to promote oral health. Howell et al., (1993) *Journal of Clinical Periodontology.* 20, 335-339.

Lantibiotic drugs have enormous potential, and will most likely be well received by the medical community. Although the market for antibiotic usage remains high and will remain so as long as there are infectious diseases, the overall lifecycle for most antibiotics is short, due to mutation and bacterial resistance. The benefits of the lantibiotic class of antibiotic drugs is that they have a proven track record of being relatively resistant to bacterial adaptation and have been found to have potent bactericidal activity against a number of bacterial pathogens resistant to other antibiotics.

All patents, patent applications, and other scientific or technical writings referred to anywhere herein are incorporated by reference in their entirety. The methods and compositions described herein as presently representative of preferred embodiments are exemplary and are not intended as limitations on the scope of the invention. Changes therein and other uses will be evident to those skilled in the art, and are encompassed within the spirit of the invention. The invention illustratively described herein suitably can be practiced in the absence of any element or elements, limitation or limitations that are not specifically disclosed herein. Thus, for example, in each instance herein any of the terms "comprising", "consisting essentially of", and "consisting of" can be replaced with either of the other two terms, without changing their customary meanings. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modification and variation of the concepts herein disclosed are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The present invention may be better understood in light of the following examples, which are intended for illustration purposes only, and should not be construed as limiting the scope of the invention in any way.

EXAMPLES

Example 1

Synthesis of Differentially Protected Orthogonal Lanthionines

A. Synthesis of Fmoc-Cys

Figure 4:
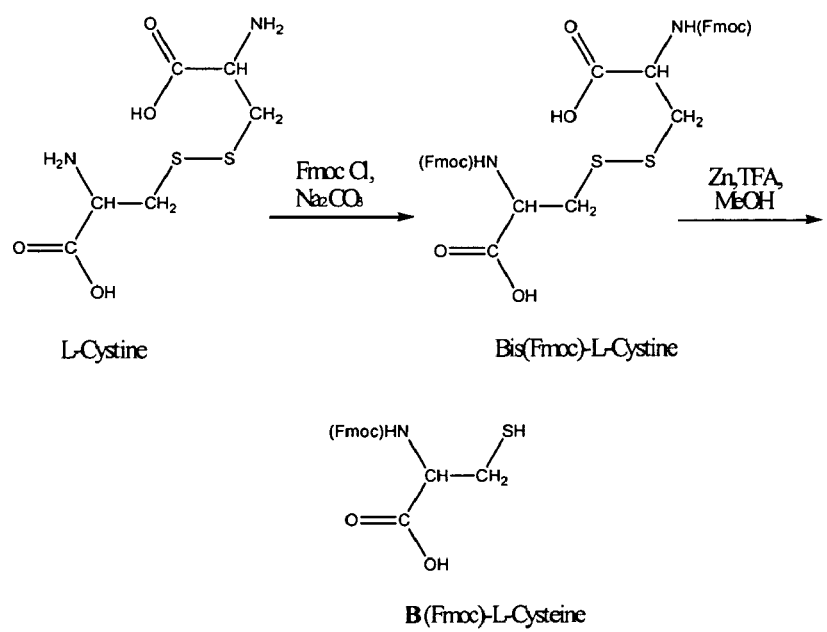
FIG. 4 shows the synthetic strategy for Fmoc-protected cysteine.

Fmoc-protected cysteine (FIG. 3, structure B) was synthesized in a two step sequence from L-cystine as outlined in FIG. 4. Sodium carbonate (4.6 g, 43.6 mmol) and L-cystine (5.0 g, 20.8 mmol) were dissolved in water (200 mL). The resulting solution was cooled to 10° C. FmocCl (11.85 g, 45.8 mmol) was dissolved in dioxane (80 mL), and the resulting solution was added dropwise to the aqueous solution of L-cystine. The solution was stirred for 2 h at 10° C. and allowed to gradually warm to room temperature. A thick white precipitate was obtained that was filtered onto a sintered glass funnel. The product was triturated with diethyl ether (50 mL) and dried in vacuuo for 2 d. N,N'-Bis(Fmoc)-L-cystine (14.0 g, 98% yield) was obtained as a white powder.

N,N'-Bis(Fmoc)-L-cystine (12.0 g, 17.5 mmol) was dissolved in methanol (300 mL). Granular zinc (12.0 g) was added to this solution and the resulting mixture was vigorously stirred using a magnetic stirrer. Trifluoroacetic acid (75 mL, 1 mol) was added dropwise into the reaction mixture over period of 2 h and stirred at room temperature for a period of 12 h. The reaction was monitored by C-18 reverse phase high pressure liquid chromatography (HPLC) and thin layer chromatography (TLC, chloroform/methanol/acetic acid=30:1: 0.1, v/v). Upon disappearance of N,N'-bis(Fmoc)-L-cystine, the reaction mixture was filtered and concentrated on a rotary evaporator to reduce the volume to approximately 100 mL. Dichloromethane (400 mL) was added and the mixture was washed with 2N aqueous hydrochloric acid. The aqueous layer was extracted with dichloromethane and the combined organic layers were dried over magnesium sulfate. Concentration of the solution gave N-(Fmoc)-L-cysteine, 8.8 g 73%) (FIGS. 3 and 4, structure B) as a white powder.

B. Synthesis of N-(Alloc)-D-Serine Propargyl Ester

Synthesis of N-(Alloc)-D-serine propargyl ester (FIG. 3, structure A) was performed as follows (see FIG. 5). D-Serine (10.5 g, 100 mmol) and sodium carbonate (11.1 g, 105 mmol) were dissolved in water (100 mL). Acetonitrile (50 mL) was added to this solution and the mixture was cooled in an ice bath to 5° C. Allyl chloroformate (11.7 mL, 13.3 g, 110 mmol) was added dropwise during period of 30 min. The reaction mixture was gradually allowed to warm to room temperature and stirred for 12 h. The mixture was concentrated under vacuum to approximately 100 mL to remove acetonitrile and the residue was cooled to 0-5° C. The pH of the solution was adjusted to 2.0 by adding concentrated aqueous HCl (approx. 10 mL). The product was extracted with ethyl acetate (5×40 mL), and the extract was dried over anhydrous magnesium sulfate. The solvent was removed on rotary evaporator under vacuum to yield N-(Alloc)-D-serine (16.9 g, 89%) which appeared as a pale yellow oil.

N-(Alloc)-D-serine (16 g, 85 mmol) was dissolved in DMF (70 mL). Sodium bicarbonate (7.9 g, 94 mmol) was added to the resulting solution. Propargyl bromide (80% in toluene, 10.5 mL, 94 mmol) was added dropwise during period of 20 min at room temperature. The reaction mixture was stirred at room temperature for 2 d. The reaction mixture was concentrated under vacuum on rotary evaporator and the residue was dissolved in ethyl acetate (100 mL). The solution was washed with aqueous sodium bicarbonate (2×50 mL) and water (2×50 mL), and dried over magnesium sulfate. The solvent was removed on a rotary evaporator under vacuum to give N-(Alloc)-D-serine propargyl ester (18 g, 93% yield).

C. Synthesis of N-(ivDde)-D-Serine (Benzyl) Ester

N-(ivDde)-D-serine (FIG. 3, structure C) was prepared from D-serine and ivDde-OH which was synthesized by O-acylation of dimedone with isovaleryl chloride in the presence of pyridine followed by the rearrangement of formed 5,5-dimethyl-3-oxocyclohex-1-enyl 3-methylbutanoate with aluminum chloride using a previously reported method (Akhrem, A. A., et al. *Synthesis* 1978, 925). In particular, a solution of isovaleryl chloride (13.5 mL, 13.3 g, 110 mmol) in dichloromethane (50 mL) was added dropwise over period of 15 min to a stirred solution of dimedone (14 g, 100 mmol) and pyridine (9.7 mL, 9.5 g, 120 mmol) in dichloromethane (150 mL). The reaction mixture was stirred for 1.5 h, and washed with 2N aqueous hydrochloric acid (2×50 mL), water, and saturated aqueous sodium bicarbonate (50 mL), and then dried over magnesium sulfate. The solvent was removed by rotary evaporator under vacuum to give 5,5-dimethyl-3-oxocyclohex-1-enyl 3-methylbutanoate (22.4 g, 100% yield) which appeared as a light yellow oil. To a stirred suspension of aluminum chloride (16.0 g, 120 mmol) in dichloromethane (100 mL) cooled on ice-bath was added dropwise a solution of 5,5-dimethyl-3-oxocyclohex-1-enyl 3-methylbutanoate (11.2 g, 50 mmol) over period of 30 min. The reaction mixture was allowed to warm to room temperature and stirred for 1 h. Then the reaction mixture was slowly poured into a mixture of 37% aqueous hydrochloric acid (50 mL) and ice (150 g) with cooling on ice so the temperature did not exceed 5° C. Brine (200 mL) was added to the mixture and the product was extracted with dichloromethane (6×50 mL, completeness of the extraction was checked by TLC). The extract was washed with brine (2×50 mL), dried over magnesium sulfate, and concentrated on rotary evaporator under vacuum. The crude product was purified by column chromatography on silica gel using gradient of hexanes going to ethyl acetate:hexanes (1:10) to give ivDde-OH (10.5 g, 94%) which appeared as a light yellow oil.

N-(ivDde)-D-serine was then synthesized as follows: To a mixture of ivDde-OH (1.1 g, 5 mmol) and D-serine (0.6 g, 5.75 mmol) in methanol (50 mL) was added N-ethyldiisopropylamine (3.4 mL, 2.6 g, 20 mmol). The reaction mixture was stirred under reflux overnight. The TLC test (ethyl acetate/hexanes 1:4) showed no free ivDde-OH. The reaction mixture was cooled to room temperature and the solvent was removed by rotary evaporation under vacuum. The residue was dissolved in water (40 mL), cooled to 5-10° C., and acidified to pH 2 by the dropwise addition of 2N aqueous hydrochloric acid. The mixture was stirred for 30 min and the precipitate was filtered, washed with water and dried in vacuum to give N-(ivDde)-D-serine (1.5 g, 96%), as white microcrystals.

N-(ivDde)-D-serine benzyl ester was prepared as follows: To a mixture of N-(ivDde)-D-serine (0.93 g, 3 mmol) and sodium bicarbonate (0.34 g, 4 mmol) in DMF (20 mL) was added benzyl bromide (0.43 mL, 0.62 g, 3.6 mmol) and the mixture was stirred at room temperature for 24 h. The mixture was concentrated under vacuum on a rotary evaporator, and the residue was dissolved in ethyl acetate (40 mL). The solution was washed with water and the aqueous layer was extracted with ethyl acetate (2×30 mL). The combined organic layer was washed with saturated aqueous sodium bicarbonate (2×40 mL), and water (40 mL). The organic layer was dried over magnesium carbonate, and the solvent was removed under vacuum on a rotary evaporator to give N-(ivDde)-D-serine benzyl ester (1.03 g, 86%), as white needles.

D. Synthesis of N-(Alloc)-D-β-Bromoalanine Propargyl Ester and N-(ivDde)-D-β-Bromoalanine Benzyl Ester The corresponding β-bromoalanine derivatives of N(alloc)-D-serine (propargyl) ester and N(ivDde)-D-serine (benzyl) ester are synthesized by dissolving one equivalent of the appropriate ester in dichloromethane (or a similar aprotic solvent) and treating the solution with one equivalent of carbon tetrabromide and triphenylphosphine. The reaction is stirred at room temperature until complete as observed by TLC, and the desired β-bromoalanine derivative is purified by flash chromatography. Alternatively, the syntheses are achieved using phosphorous tribromide in a solvent such as toluene or dichloromethane followed by mild basic workup to afford the desired D-β-bromoalanines. Besides bromylation, tosylation or other leaving groups may be used in the alkylation step described below to produce the final protected lanthionine.

E. Synthesis of Lanthionines 1 and 2

Lanthionine 1 is synthesized through the alkylation of N(alloc)-D-β-bromoalanine propargyl ester with (Fmoc)-L-cysteine (FIG. 5). Lanthionine 2 is synthesized through the alkylation of N(ivdDe)-D-β-bromoalanine benzyl ester with (Fmoc)-L-cysteine (FIG. 6).

The respective β-bromoalanine is alkylated with (Fmoc)-L-cysteine as follows: one equivalent of the β-bromoalanine is dissolved in dichloromethane (or a similar aprotic solvent) and treated with (Fmoc) cysteine under phase transfer catalysts such as tetrabutylammonium bromide, tetrabutyl ammonium iodide, or Aliquat 336. The amount of the catalyst required is 5-50 mol % and can be optimized to obtain a good rate of reaction and clean formation of product. Reaction temperature can also be optimized within a range of 10-50° C.

The product thus obtained is purified by flash column chromatography; and the purity and identity of the product is determined by NMR, HPLC, mass spectrometry and/or TLC. The synthetic routes to Lanthionines 1 and 2 are relatively straightforward, and the products are expected to be stable so that scale up and bulk synthesis (>10 g) can be easily accomplished.

Example 2

Synthesis of Lantibiotic Nisin A Analog Using Lanthionines 1 and 2

A. Solid Phase Peptide Synthesis of the Nisin A Analog

A Nisin A analog [SEQ ID NO: 2] is synthesized in accordance with the invention as outlined below. The analog contains alanine substitutions for the dehydrobutarine at position 33 and dehydroalanines at position 30 and 2. Considerable evidence indicates that this will have no significant effect on the spectrum of activity and potency of the product relative to native Nisin A (Kuipers et al., (1996); Devos et al. (1995), *Molecular Microbiology* 17, 427-437; Sahl et al. (1995), *European Journal of Biochemistry* 230, 827-853; Bierbaum et al. (1996), *Applied and Environmental Microbiology* 62, 385-392).

Unless otherwise indicated, all protocols are standard Fmoc SPPS methodology reported in the literature. White (2003) *Fmoc Solid Phase Peptide Synthesis, A practical Approach*, Oxford University Press, Oxford. Nisin A is synthesized from its carboxy terminus in a stepwise fashion (see FIG. 1).

1. The carboxyl of $N^\alpha$-Fmoc-Lys-$N^\in$-t-butyloxycarbonyl-L-lysine (Residue 1) is attached to CLEAR-Acid Resin™ (Peptide International). The resin is checked with ninhydrin to verify the completion of the reaction.
2. Deprotection of the Fmoc group situated on the amide of the lysine is achieved using 20% piperidine in DMF at room temperature.
3. The above steps (1-2) of coupling and deprotection are repeated to attach, in order, alanine, valine, histidine, isoleucine and serine (residues 2 through 6) using the respective Fmoc L-amino acids (commercially available). Amino acids such as histidine, lysine and serine have t-butyl groups attached to their reactive side chains to protect these groups.
4. The next coupling is performed using orthogonal lanthionine 1 after which the Fmoc group on orthogonal lanthionine 1 is removed using 20% piperidine in DMF.
5. The Fmoc histidine (residue 8) is coupled.
6. The Fmoc histidine is deprotected with 20% piperidine in DMF and the histidine is coupled with orthogonal lanthionine 2.
7. The propargyl group on orthogonal lanthionine 1 is cleaved using dicobalt-octacarbonyl in dichloromethane. The Fmoc amino terminus of orthogonal lanthionine 2 is unmasked using 20% piperidine in DMF. The unmasked C-terminus of orthogonal lanthionine 1 and the unmasked N-terminus of orthogonal lanthionine 2 are coupled. Synthesis of ring E is complete at this step.
8. The N(Alloc) group of lanthionine 1 is removed by treating the peptidyl resin twice with 20 mol % of Pd(PPh$_3$)$_4$ and 20-25 equivalents of PhSiH$_3$ in dichloromethane for 15-20 minutes.
9. The unmasked N-terminus is coupled with Fmoc alanine (residue 11). The Fmoc group on alanine is deprotected using 20% piperidine in DMF.
10. The remaining C-terminus of lanthionine 2 is deprotected using a transfer hydrogenation protocol using palladium on charcoal and cyclohexadiene in dichloromethane.
11. The unmasked C-terminus of lanthionine 2 and the N-terminus of alanine (residue 11) is coupled. Synthesis of overlapping rings E and D is complete at this step. In order to check that the correct product is synthesized, a small amount of the resin is taken and the peptide is cleaved using a cleavage cocktail (see below). The resulting peptide is analyzed by Maldi and LC-MS.
12. The ivDde on lanthionine 2 is removed using 2-10% hydrazine in DMF and the resulting free amino terminus is elongated sequentially with Fmoc protected lysine, methionine and asparagine (residues 13, 14 and 15).
13. Lanthionine 1 is attached to the deprotected N-terminus of asparagines. (Either lanthionine 1 or lanthionine 2, however, can be used to complete the synthesis of rings C, B and A.)
14. The Fmoc group of lanthionine 1 is deprotected and coupled sequentially with Fmoc glycine, methionine, alanine, leucine and glycine (residues 17 through 21) to form ring C.
15. The propargyl group at the C-terminus of lanthionine 1 is removed using 1 equivalent of dicobaltoctacarbonyl and coupled to the N-terminus of glycine (residue 21), completing ring C.
16. The Alloc group on N terminus of lanthionine 1 is removed according to the procedure described in step 8 and coupled to Fmoc lysine (residue 23).
17. The N-terminus of lysine is deprotected, and lanthionine 1 is coupled to the N-terminus of lysine.
18. The Fmoc group of lanthionine 1 is deprotected and sequentially coupled with Fmoc glycine and Fmoc proline (residues 25 and 26).
19. The propargyl group at the C-terminus of lanthionine 1 is removed using 1 equivalent of dicobaltoctacarbonyl and coupled to the deprotected N-terminus of proline thus forming ring B.
20. The Alloc group on the N terminus of lanthionine 1 is removed according to the procedure described above and coupled to lanthionine 1.
21. The Fmoc group of lanthionine 1 is deprotected and sequentially coupled with the Fmoc leucine, alanine, and isoleucine (residues 29 through 31).
22. The propargyl group at the C-terminus of lanthionine 1 is removed using 1 equivalent of dicobaltoctacarbonyl and coupled to the deprotected N-terminus of isoleucine, thus forming ring A.
23. The Alloc group on the N terminus of lanthionine 1 is removed according to the procedure described above and sequentially coupled to Fmoc alanine and isoleucine (residues 33 and 34). This completes the synthesis of the Nisin A analog.

B. Cleavage of the Synthesized Peptide from the Resin

Because the synthesized peptide contains significant amounts of sulfur, a cocktail containing TFA/thioanisole/water/phenol/ethanedithiol (82.5/5/5/5/2.5) is used to cleave the peptide from the resin (White 2003). The resin is thoroughly washed with dichloromethane to remove traces of DMF and other residual organics and treated with the above cocktail. Optimization of the time point for cleavage is achieved by carrying out the reaction on 15-20 mg of the resin followed by LC-MS at hourly intervals for up to 18 hours. Optimized conditions are used to scale up the cleavage. The cleaved peptide is gradually poured into cold ether, thus precipitating the peptide. The precipitated peptide is washed with cold ether and dried.

C. Purification of the Cleaved Peptide

The peptide is purified by reconstituting it in water containing 1% TFA. The solution is subjected to HPLC on a C-18 reverse phase column using a gradient of acetonitrile:water and a Biorad HPLC with a quadtech detector. The peaks are collected and analyzed by Maldi tof to confirm the identity of the product. The fractions containing the desired peptide are collected and lyophilized to obtain the purified product. Purity is determined using HPLC, MS and NMR.

Example 3

Structural and Biological Analysis of the Purified Nisin A Analog

A. Bioassay of the Nisin A Analog

The lantibiotic thus synthesized and purified as shown in Examples 1 and 3 are aliquoted and lyophilized. The resulting product is weighed and the final yields calculated. The biological activity of the Nisin A analog is determined by a deferred antagonism assay, known in the art, which permits the determination of the minimum inhibitory and bacteriocidal concentrations of the Nisin A analog (Hillman et. al. (1984), *Infection and Immunity* 44, 141-144; Hillman et. al. (1998), *Infection and Immunity* 66, 2743-2749). Comparison to native Nisin A to enables the determination of the respective specific activities. The bioassay is conducted as follows:

Samples (20 μl) of fractions to be tested for Nisin A activity are serially diluted 2-fold using acetonitrile: water (80:20) in 96 well microtiter plates. Concentrations range from 20 to 0.08 μg/mL. An overnight culture of the *Micrococcus luteus* strain ATCC272LS (spontaneously resistant to 100 ug/mL streptomycin) is diluted 1:1000 (ca. $10^6$ cfu/mL) in Trypticase soy broth (Difco) and grown at 37° C. to an $OD_{600}$=0.2. Six hundred microliters of cells are added to 15 mL of Trypticase soy broth top agar (0.75% agar) that has been cooled to 45° C., and poured over the surface of a large Petri dish containing Trypticase soy agar containing 100 μg/mL streptomycin (the streptomycin prevents the outgrowth of contaminants that may be present without affecting the ability to determine the amount of Nisin A activity present). After the top agar has set, 5 μL samples of the serial 2-fold dilutions of the fractions to be tested are spotted onto the surface of the plates and allowed to air dry.

The plates are incubated at 37° C. for 24 hours and examined for zones of growth inhibition of the indicator strain. The titer of the sample is taken as the reciprocal of the highest dilution that produces visible inhibition of growth of the *M. luteus* indicator strain. As a control, authentic Nisin A is diluted and spotted as described above. Concentrations range from 20 to 0.08 μg/mL. The results enable a determination of the bioactivity of the synthetic analog relative to native Nisin A as a percentage based on the levels of purity of these compounds as established in the previous step.

The above bioassay using the synthetic and native Nisin A is conducted for at least a dozen species of gram positive species including multidrug resistant *Staphylococcus aureus, Enterococcus faecalis,* and *Listeria monocytogenes*. One or more other antibiotics appropriate for the target species being tested are also run in parallel for comparison.

B. Structural Analysis of the Nisin A Analog

The three dimensional structure of the Nisin A analog is determined by comparison to native Nisin A using TOSCY and NOESY NMR. Samples (3-5 mM) of the synthetic and native Nisin A are prepared in $H_2O/D_2O$/3-(trimethylsilyl)-propionic acid-D4, sodium salt (TSP) (90.0:9.9:0.1%) in a total volume of 700 μL. The NMR data is collected on a 600 MHz with cryoprobe Bruker Avance spectrometer at 25° C. and the carrier frequency is centered on the water resonance, which is suppressed by presaturation during a 1.5 sec relaxation delay. The TOCSY experiments are acquired with a 60 ms mixing time using the MLEV-17 sequence (Bax & Davis (1985), *Journal of Magnetic Resonance* 65, 355-360). The NOESY experiments are acquired with 200 ms, 400 ms, and 450 ms mixing times. The delay times to create or refocus antiphase coherence in the HMQC and HMBC experiments are adjusted to 3.5 ms (140 Hz coupling) and 60 ms (8.5 Hz coupling), respectively.

All 2D data is collected with 2048 complex points in the acquisition dimension and between 256 and 512 complex points for the indirect dimensions. Phase sensitive indirect detection for all experiments is achieved using the method of States-TPPI (Marion et. al. (1989), *Journal of Magnetic Resonance* 85, 393-399). $^1H$ chemical shifts are referenced to TSP. Data is processed with NMRpipe (Delaglio et. al. (1995), *Journal of Biomolecular NMR* 6, 277-293) by first removing the residual water signal by deconvolution, multiplying the data in both dimensions by a squared cosine function or a squared cosine function with a 60° shift (for the $^1H$ dimension of HMBC), zerofilling once, Fourier transformation, and baseline correction. Data is analyzed with the interactive computer program NMRView (Johnson & Blevins (1994), *Journal of Biomolecular Nmr* 4, 603-614). The $^1H$ resonances are assigned according to standard methods (Wüthrich, K. (1986) *NMR of Proteins and Nucleic Acids.,* Wiley, New York) using TOCSY (Braunschweiler & Ernst (1983), *Journal of Magnetic Resonance* 53, 521-528) and NOESY (Kumar et. al. (1980), *Biochem. Biophys. Res. Commun.* 95, 1-6) experiments. HMQC (Bax et. al. (1983), *Journal of Magnetic Resonance* 55, 301-315; Muller (1979), *Journal of the American Chemical Society* 101, 4481-4484) and HMBC (Bax & Summers (1986), *Journal of the American Chemical Society* 108, 2093-2094) experiments are used to clarify some areas of ambiguity in the TOCSY and NOESY spectra.

The lysine, isoleucine, leucine, glycine, and asparagine residues have distinct and easily characterized $^1H$ resonance spin patterns, which make them easy to assign in the 2D TOCSY and NOESY experiments. These residues are identified first. The thioether linkage patterns are verified via long range beta proton NOE connectivity patterns. Long range NOEs are presumably identifiable between residues at positions 3 and 7, 8 and 11, 13 and 19, 23 and 26, and 25 and 28. Long range NOEs ($>i^{+2}$) are used for 3-dimensional modeling as described in Smith et. al., 2002 (*Structural and Functional Characterization of the Lantibiotic Mutacin* 1140, University of Florida, Gainesville).

NOE cross-peak intensities are measured in NMRView. Distances are calibrated using the relationship $r_{ab}^6 = r_{cal}^6 (V_{cal}/V_{ab})$, where $r_{ab}$ is the distance between atoms a and b, $V_{ab}$ is the NOESY a to b cross-peak volume, $r_{cal}$ is a known distance, and $V_{cal}$ is the corresponding volume of the NOESY calibration cross-peak. The distance used for calibrations is the beta protons of the isoleucine. Only the interresidue NOE cross-peaks are used as distance restraints in calculations. The energy wells are defined using an upper and lower force constant of 1 kcal/mol/Å$^2$.

All conformational modeling is performed using InsightII software (Accerlys, San Diego, Calif.). The molecular dynamic simulations are run in a vacuum at 500K with a dielectric constant of 4.0 using the cvff force field with cross-terms, Morse potentials, and 40 Å cutoff distances. The peptide is constructed using the builder function in InsightII. Initially, the linear peptide is minimized, and then unrestrained molecular dynamics are run for 10 ps. After this, only the distance restraints of i+2 or greater are added. The molecular dynamic simulations are stopped periodically when the i+2 or greater distance restraints are satisfied among the residues that make up each thioether ring. Ring A is formed first followed by ring B and ring C and then intertwined rings D and E. Once the thioether rings are formed, the i+1 distance restraints are added to the i+2 or greater distance restraints, and the molecular dynamic simulation is run for 5 ns at 500K with a dielectric constant of 4.0 using cvff force field with cross terms and Morse potentials. Molecular dynamic simulations are then run for another 20 ns with all the restraints.

History files from the dynamics are written every 10 ps. Two-hundred structures from the history file starting at 1 ns and spaced every 100 ps are energy minimized with all the NMR restraints using 2000 steps of steepest decent followed by conjugate gradients and Newton-Raphson until the root-mean-square (RMS) gradient of the energy of 0.01 kcal/mol/Å is reached. The 200 energy minimized structures are checked for NMR restraint violations using PROCHECK-NMR software (Laskowski, R. A., Rullmann, J. A. C., MacArthur, M. W., Kaptein, R. & Thornton, J. M. (1996) AQUA and PROCHECK-NMR: Programs for checking the quality of protein structures solved by NMR, *Journal of Biomolecular Nmr.* 8, 477-486). The energy minimized structures are grouped into families using the XCluster program (Shenkin, P. S. & McDonald, D. Q. (1994) Cluster-Analysis of Molecular-Conformations, *Journal of Computational Chemistry.* 15, 899-916). The conformations are compared to the native structures of Nisin A determined by VanDeVen et. al., 1991 (*European Journal of Biochemistry* 202, 1181-1188).

We claim:

1. A method of synthesizing an intramolecularly bridged polypeptide comprising two overlapping intramolecular bridges comprising:

(a) covalently binding the free carboxy terminus of a first differentially protected orthogonal intramolecular bridge of formula

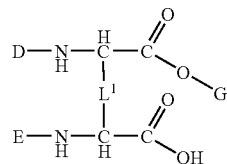

to a solid support or to the free amino terminus of an amino acid or polypeptide optionally bound to a solid support and wherein in each instance $L^1$ represents covalently bound amino acid side chains, wherein D, E, and G are protecting groups, each of which is selectively removed under different reaction conditions, and wherein the reaction conditions for the removal of protecting group D are different from those for the removal of the amino protecting groups of amino acids of the remainder of the polypeptide chain;

b) removing protecting group E to form a free amino terminus;

c) adding an amino-protected amino acid to the free amino terminus and then deprotecting the amino acid to yield a new free amino terminus;

d) optionally repeating c) one or more times;

e) covalently binding the free carboxy terminus of a second differentially protected orthogonal intramolecular bridge of formula

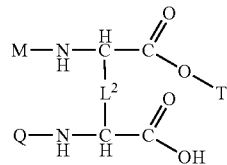

to the free amino terminus, wherein $L^2$ is as defined as $L^1$ above, wherein M, Q, and T are protecting groups, each of which is selectively removed under different reaction conditions, wherein D and M are removed only under different conditions, wherein G and T are removed only under different conditions, wherein the reaction conditions for the removal of protecting group M are different from those for the removal of the amino protecting groups of the amino acids of the remainder of the polypeptide chain, and wherein E and Q are removed under conditions different from those that will remove D and those that will remove M; f) removing protecting group Q to form a free amino terminus; g) optionally adding an amino-protected amino acid to the free amino terminus and then deprotecting the amino acid to yield a new free amino terminus;

h) optionally repeating g) one or more times;

i) removing protecting group G of the first differentially protected orthogonal intramolecular bridge to form a free carboxy-terminus;

j) coupling the free carboxy-terminus to the free amino terminus;

k) removing protecting group D of the first differentially protected orthogonal intramolecular bridge to form a free amino terminus;

l) optionally adding an amino-protected amino acid to the free amino terminus and then deprotecting the amino acid to yield a new free amino terminus;

m) optionally repeating l) one or more times;

n) removing protecting group T of the second differentially protected orthogonal intramolecular bridge forming a free carboxy-terminus;

o) coupling the free carboxy-terminus to the free amino terminus;

p) removing protecting group M of the second differentially protected orthogonal intramolecular bridge to form a free amino terminus; and q) optionally adding an amino-protected amino acid to the free amino terminus and then deprotecting the amino acid to yield a new free amino terminus; and r) optionally repeating q) one or more times.

2. The method of claim 1 further comprising:

a) coupling a differentially protected orthogonal intramolecular bridge of formula

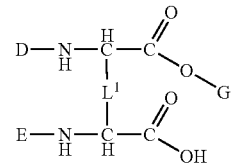

to the free amino terminus, wherein in each instance $L^1$ represents covalently bound amino acid side chains, wherein D, E, and G are protecting groups, each of which are selectively removed under different reaction conditions, and wherein the reaction conditions for the removal of protecting group D are different from those for the removal of the amino protecting groups of the amino acids of the remainder of the polypeptide chain;

b) removing protecting group E to form a free amino terminus;

c) adding an amino-protected amino acid to the free amino terminus and then deprotecting the amino acid to yield a new free amino terminus;

d) optionally repeating c) one or more times;

e) removing protecting group G to form a free carboxy terminus;

f) coupling the free carboxy terminus of e) to the free amino terminus;

g) removing protecting group D to form a free amino terminus;

h) optionally adding an amino-protected amino acid to the free amino terminus and then deprotecting the amino acid to yield a new free amino terminus;

i) optionally repeating h) one or more times; and j) optionally repeating steps a)-i).

3. The method of claim 1 wherein the differentially protected orthogonal intramolecular bridges are lanthionines.

4. The method of claim 1 wherein the intramolecularly bridged polypeptide is a lantibiotic.

5. The method of claim 1 wherein D, E, M, and Q are selected from Fmoc, Alloc, and IvDde.

6. The method of claim 1 wherein G and T are selected from the group consisting of propargyl ester and benzyl ester.

7. The method of claim 3 wherein the intramolecular bridges are selected from the group consisting of β-methyl-lanthionine (MeLan), S-[(Z)-2-Aminovinyl]-D-cysteine (AviCys), and S-[(Z)-2-Aminovinyl]-2-methyl-D-cysteine.

8. The method of claim 4 wherein the lantibiotic is selected from the group consisting of Nisin A, Nisin Z, Subtilin, Ericin S, Ericin A, Streptin, Epidermin, [Val1-Leu6]-epidermin, Gallidermin, Mutacin 1140, Mutacin B-Ny266, Mutacin III, Mutacin I, Pep5, Epilancin K7, Epicidin 280, Lacticin 481, Variacin, Mutacin II, StreptococcinA-FF22, SalivaricinA, [Lys2-Phe7]-salivaricin A, Plantaricin C, Sublancin 168, Butyrivibriocin OR79A, Cinnamycin, Duramycin, Duramycin B, Duramycin C, Curamycin C, Ancovenin, Mersacidin, Actagardine, Ala(0)-actagardine, Subtilocin A, Lacticin 3147A1, Lacticin 3147A2, Staphylococcin C55α, Staphylococcin C55β, Plantaricin Wα, Plantaricin Wβ, Cytolysin $L_L$, and Cytolysin $L_S$.

9. The method of claim 8 wherein the lantibiotic is Nisin A or an analog thereof.

10. The method of claim 1 wherein $L^1$ or $L^2$ comprises a bond selected from the group consisting of a thioether, a disulfide, an amide or an ether.

\* \* \* \* \*

SEQUENCE LISTING

```
<160> NUMBER OF SEQ ID NOS: 2

<210> SEQ ID NO 1
<211> LENGTH: 34
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa is Dhb
<220> FEATURE:
<221> NAME/KEY: MISC_FEATURE
<222> LOCATION: (5)..(5)
<223> OTHER INFORMATION: Xaa is Dha
<220> FEATURE:
<221> NAME/KEY: MOD_RES
<222> LOCATION: (8)..(8)
<223> OTHER INFORMATION: Abu
<220> FEATURE:
<221> NAME/KEY: MOD_RES
<222> LOCATION: (13)..(13)
<223> OTHER INFORMATION: Abu
<220> FEATURE:
<221> NAME/KEY: MOD_RES
<222> LOCATION: (23)..(23)
<223> OTHER INFORMATION: Abu
<220> FEATURE:
<221> NAME/KEY: MOD_RES
<222> LOCATION: (25)..(25)
<223> OTHER INFORMATION: Abu
<220> FEATURE:
<221> NAME/KEY: MISC_FEATURE
<222> LOCATION: (33)..(33)
<223> OTHER INFORMATION: Xaa is Dha

<400> SEQUENCE: 1

Ile Xaa Ala Ile Xaa Leu Ala Xaa Pro Gly Ala Lys Xaa Gly Ala Leu
1               5                   10                  15

Met Gly Ala Asn Met Lys Xaa Ala Xaa Ala His Ala Ser Ile His Val
            20                  25                  30

Xaa Lys

<210> SEQ ID NO 2
<211> LENGTH: 34
<212> TYPE: PRT
<213> ORGANISM: Artificial
<220> FEATURE:
<223> OTHER INFORMATION: Synthetic peptide

<400> SEQUENCE: 2

Ile Ala Ala Ile Ala Leu Ala Ala Pro Gly Ala Lys Ala Gly Ala Leu
1               5                   10                  15
```

```
Met Gly Ala Asn Met Lys Ala Ala Ala His Ala Ser Ile His Val
            20              25              30
Ala Lys
```